United States Patent
Stein et al.

(10) Patent No.: US 11,865,078 B2
(45) Date of Patent: Jan. 9, 2024

(54) MEDICATION APPARATUS

(71) Applicant: Digital Medical Technologies, LLC, New York, NY (US)

(72) Inventors: Joshua D. Stein, New York, NY (US); Michael C. Morena, New York, NY (US); John W. Langhauser, New York, NY (US); John D. Gusz, New York, NY (US)

(73) Assignee: DIGITAL MEDICAL TECHNOLOGIES, LLC, New York, NY (US)

( * ) Notice: Subject to any disclaimer, the term of this patent is extended or adjusted under 35 U.S.C. 154(b) by 118 days.

(21) Appl. No.: 16/336,199

(22) PCT Filed: Sep. 28, 2017

(86) PCT No.: PCT/US2017/053888
§ 371 (c)(1),
(2) Date: Mar. 25, 2019

(87) PCT Pub. No.: WO2018/064260
PCT Pub. Date: Apr. 5, 2018

(65) Prior Publication Data
US 2019/0224077 A1 Jul. 25, 2019

Related U.S. Application Data

(60) Provisional application No. 62/414,261, filed on Oct. 28, 2016, provisional application No. 62/407,656, (Continued)

(51) Int. Cl.
*A61J 7/04* (2006.01)
*G16H 20/13* (2018.01)
(Continued)

(52) U.S. Cl.
CPC .......... *A61J 7/0076* (2013.01); *A61J 7/0427* (2015.05); *G07F 11/62* (2013.01);
(Continued)

(58) Field of Classification Search
CPC ............... B65D 77/0486; B65D 77/04; B65D 77/0493; A61J 1/00; G16H 20/13; G07F 17/0092
See application file for complete search history.

(56) References Cited

U.S. PATENT DOCUMENTS 5,099,998 A * 3/1992 Curzon .................. B65D 25/34
206/514
5,197,602 A * 3/1993 Biesecker .......... B65D 77/0493
206/499
(Continued)

FOREIGN PATENT DOCUMENTS

CN 2439406 Y 7/2001
CN 2735679 Y 10/2005
(Continued)

OTHER PUBLICATIONS

International Search Report dated Jan. 30, 2018 for International Application No. PCT/US2017/053888, filed Sep. 28, 2017, (6 pgs.).
(Continued)

*Primary Examiner* — Timothy R Waggoner
(74) *Attorney, Agent, or Firm* — Mintz, Levin, Cohn, Ferris, Glovsky and Popeo, P.C.

(57) ABSTRACT

An apparatus can include a container that is configured to be closed with a cap and a cartridge for housing medication configured to be inserted within the container. The cap can include a cap sensor element configured to detect whether the container has not been activated within a predetermined period of time. The container can generate an alert based on the cap sensor detecting whether the container has not been activated within the predetermined period of time and
(Continued)

whether a preset quantity of medication has not been withdrawn from the cartridge at a preset time.

14 Claims, 19 Drawing Sheets

Related U.S. Application Data filed on Oct. 13, 2016, provisional application No. 62/400,728, filed on Sep. 28, 2016.

(51) Int. Cl.
| | | |
|---|---|---|
| *A61J 7/00* | (2006.01) | |
| *G08B 21/24* | (2006.01) | |
| *G07F 17/00* | (2006.01) | |
| *G07F 11/62* | (2006.01) | |

(52) U.S. Cl.
CPC ......... *G07F 17/0092* (2013.01); *G08B 21/24* (2013.01); *G16H 20/13* (2018.01); *A61J 2200/30* (2013.01); *A61J 2200/70* (2013.01)

(56) References Cited

U.S. PATENT DOCUMENTS

| | | | |
|---|---|---|---|
| 5,745,366 A | 4/1998 | Higham et al. | |
| 5,905,653 A | 5/1999 | Higham et al. | |
| 7,497,351 B2 * | 3/2009 | Amundson | A47K 10/421 |
| | | | 221/96 |
| 7,928,835 B1 | 4/2011 | Jovanov et al. | |
| 8,754,769 B2 | 6/2014 | Stein et al. | |
| 9,579,264 B1 * | 2/2017 | Litton | A61J 7/0481 |
| 9,901,515 B2 * | 2/2018 | Roberts | A61J 7/0463 |
| 10,751,239 B2 * | 8/2020 | Volek | A47B 31/00 |
| 10,807,773 B2 * | 10/2020 | Bois | A61J 1/03 |
| 10,829,271 B1 * | 11/2020 | Bulla | B65D 77/0493 |
| 11,036,831 B1 * | 6/2021 | Mok | G16H 40/67 |
| 2002/0162847 A1 * | 11/2002 | Roy | A47F 1/08 |
| | | | 221/92 |
| 2008/0105588 A1 | 5/2008 | Tran et al. | |
| 2008/0162183 A1 * | 7/2008 | Sachanandani | G16H 10/20 |
| | | | 705/2 |
| 2009/0134181 A1 * | 5/2009 | Wachman | G16H 20/13 |
| | | | 220/200 |
| 2010/0305975 A1 * | 12/2010 | Daya | G16H 40/67 |
| | | | 220/500 |
| 2012/0006847 A1 * | 1/2012 | Coe | G16H 40/67 |
| | | | 222/52 |
| 2012/0101630 A1 * | 4/2012 | Daya | G16H 50/20 |
| | | | 700/231 |
| 2012/0193246 A1 * | 8/2012 | Chang | B65D 81/266 |
| | | | 206/204 |
| 2012/0235550 A1 | 9/2012 | Santmyer et al. | |
| 2013/0220844 A1 * | 8/2013 | Logel | B65D 81/266 |
| | | | 206/204 |
| 2014/0098645 A1 * | 4/2014 | Mularczyk | A61J 7/0481 |
| | | | 368/10 |
| 2015/0034587 A1 * | 2/2015 | Thomson | E04D 1/24 |
| | | | 52/551 |
| 2016/0026773 A1 * | 1/2016 | Chu | G01L 5/00 |
| | | | 705/2 |
| 2016/0212389 A1 * | 7/2016 | Mehrotra | A61J 1/1418 |
| 2017/0109493 A1 * | 4/2017 | Hogg | G16H 10/60 |
| 2017/0361989 A1 * | 12/2017 | Moffett, III | B65D 25/36 |
| 2022/0301678 A1 * | 9/2022 | Zhang | A61B 5/7275 |

FOREIGN PATENT DOCUMENTS

| | | |
|---|---|---|
| CN | 102137795 A | 7/2011 |
| CN | 202457233 U | 10/2012 |
| CN | 102862774 A | 1/2013 |
| CN | 202953258 U | 5/2013 |
| CN | 104000726 A | 8/2014 |
| CN | 204106443 U | 1/2015 |
| CN | 104757789 A | 7/2015 |
| CN | 104970965 A | 10/2015 |
| CN | 105160199 A | 12/2015 |
| CN | 105264565 A | 1/2016 |
| CN | 105701356 A | 6/2016 |
| JP | 2002-516228 A | 6/2002 |
| JP | 2006230842 A | 9/2006 |
| JP | 2010-042136 A | 2/2010 |
| JP | 2011-200677 A | 10/2011 |
| JP | 2015-047390 A | 3/2015 |
| JP | 2016123804 A | 7/2016 |
| WO | WO 98/26746 A2 | 6/1998 |
| WO | WO 99/60982 A2 | 12/1999 |
| WO | 2012110700 A | 8/2012 |
| WO | 2015031472 A | 3/2015 |
| WO | 2018064260 A | 4/2018 |

OTHER PUBLICATIONS

Written Opinion of the International Searching Authority for International Application No. PCT/US2017/053888, filed Sep. 28, 2017 (10 pgs.).

* cited by examiner

FIGURE 1A
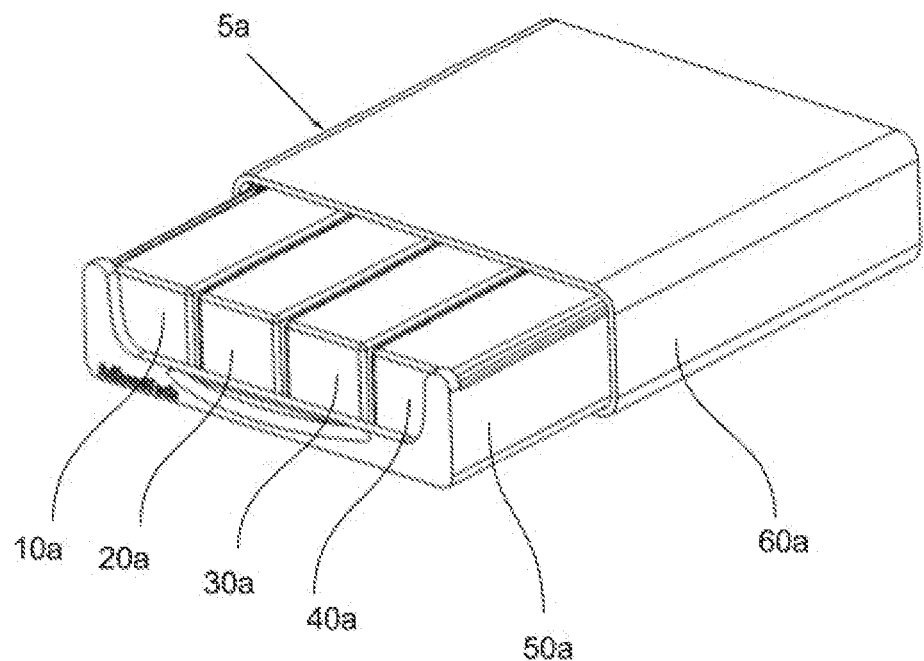
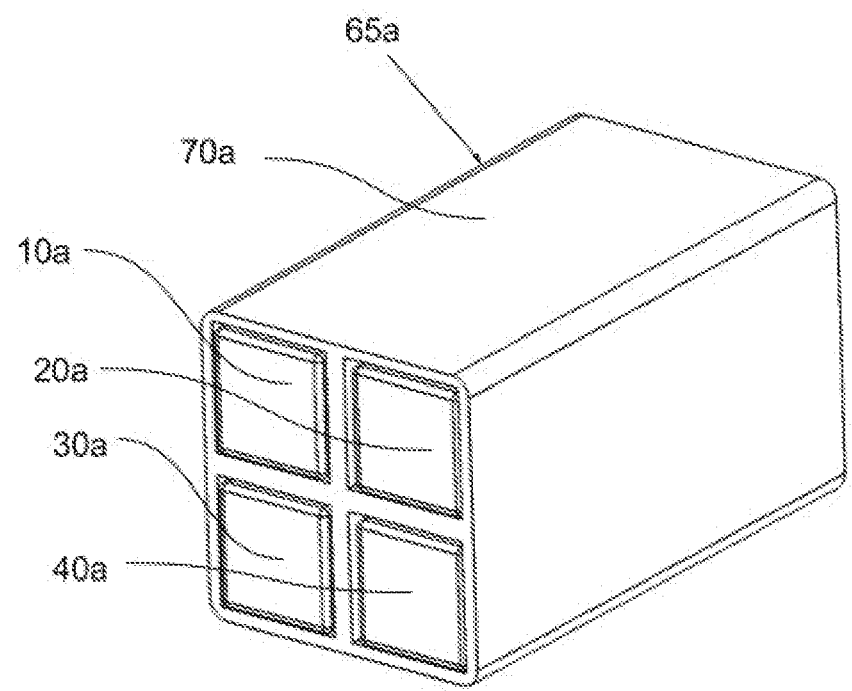
FIGURE 1B

FIGURE 2A
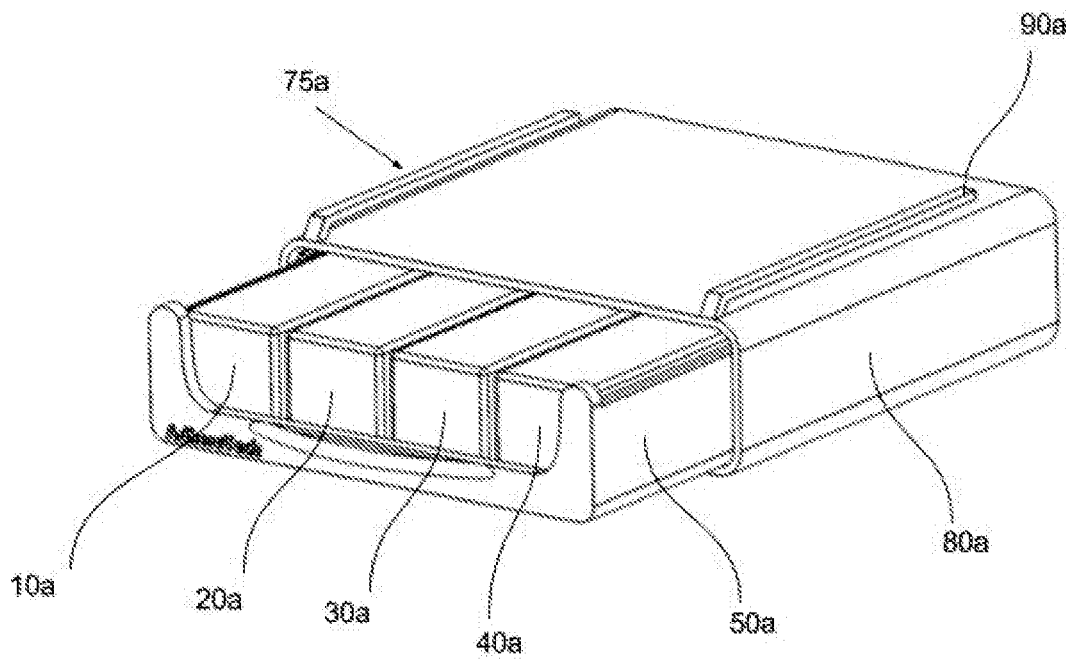
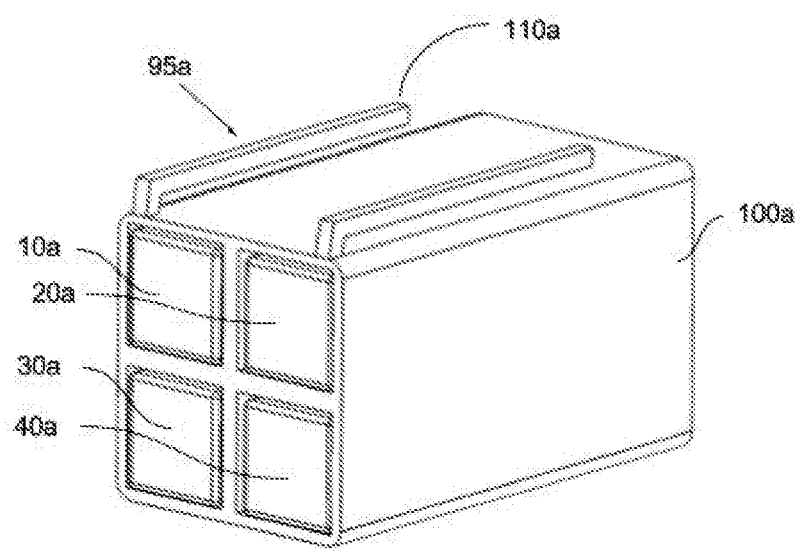
FIGURE 2B

FIGURE 4A
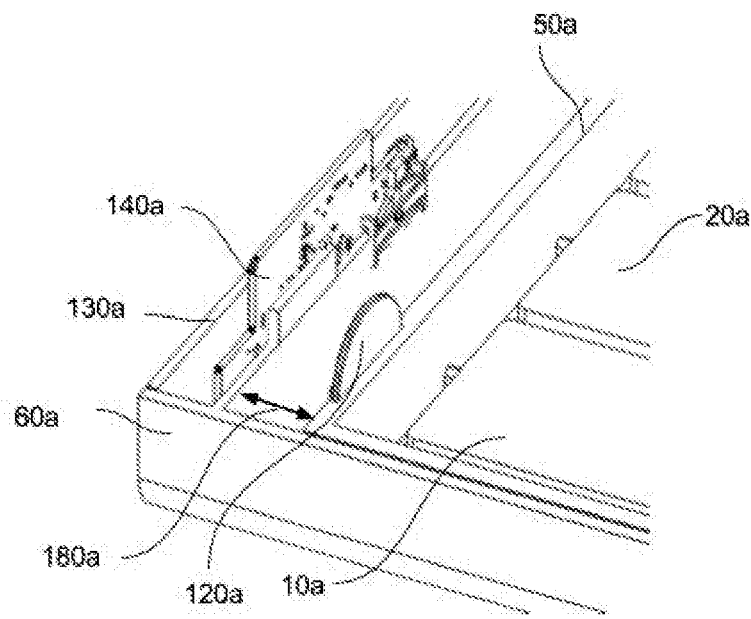
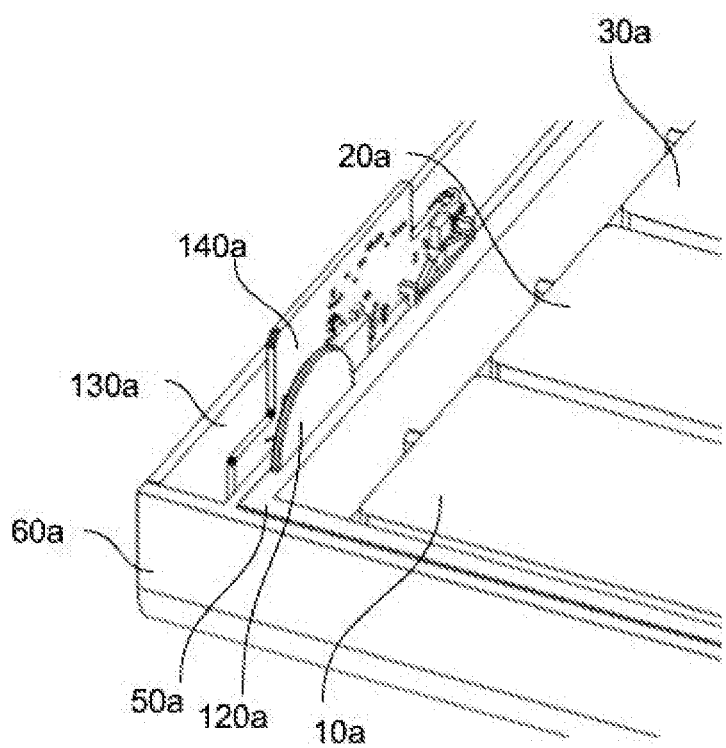
FIGURE 4B

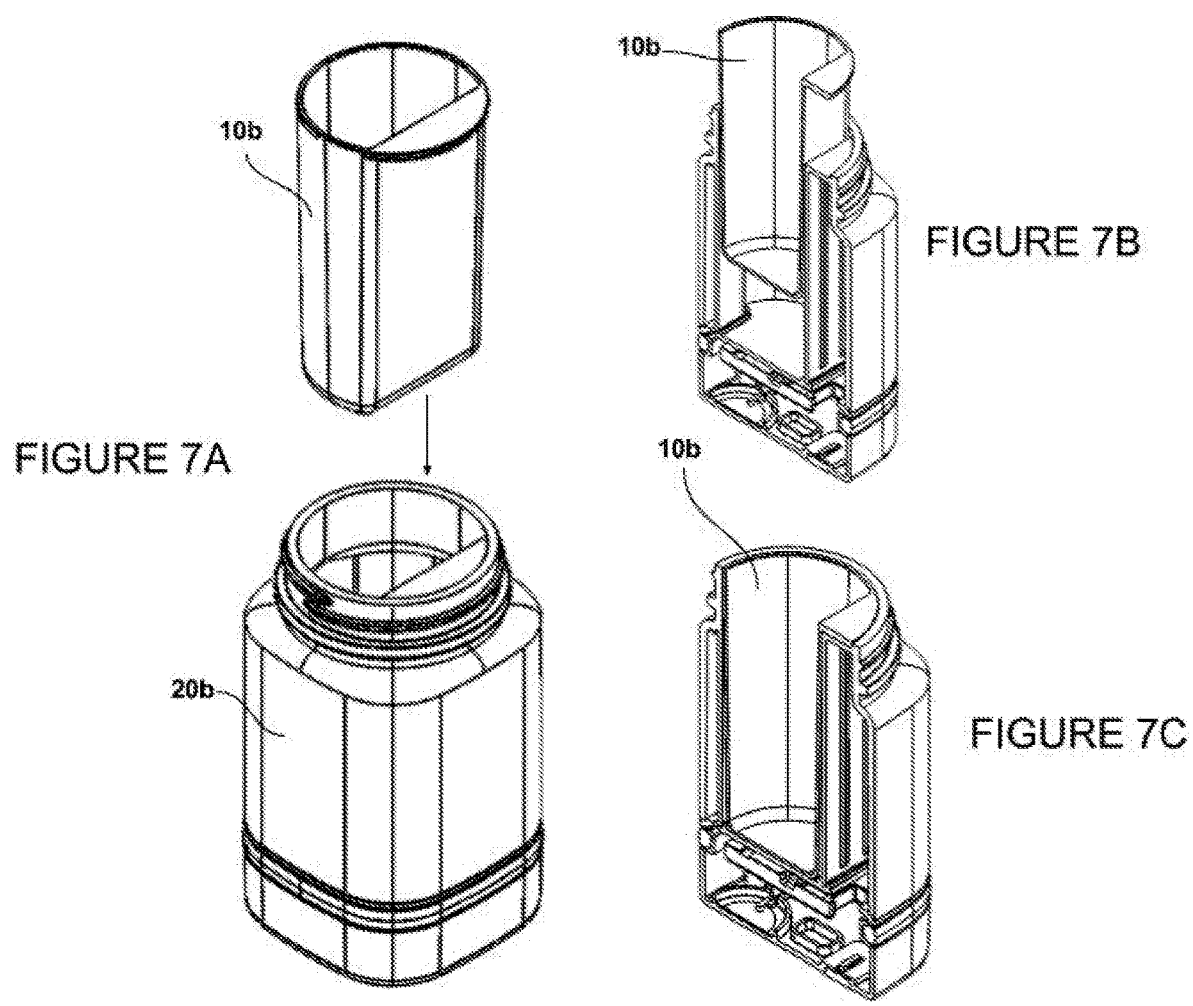

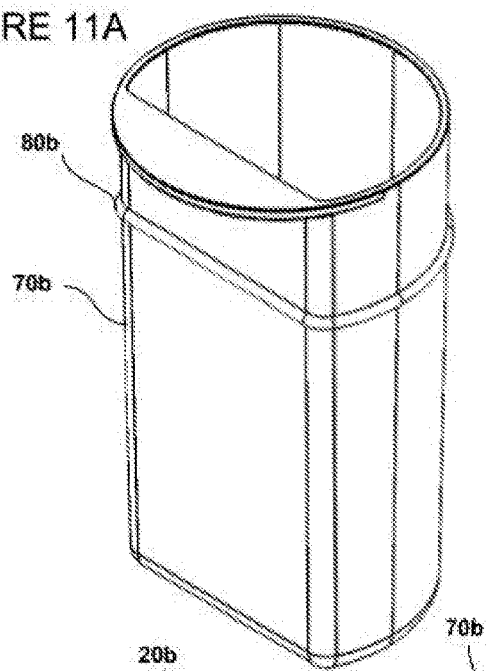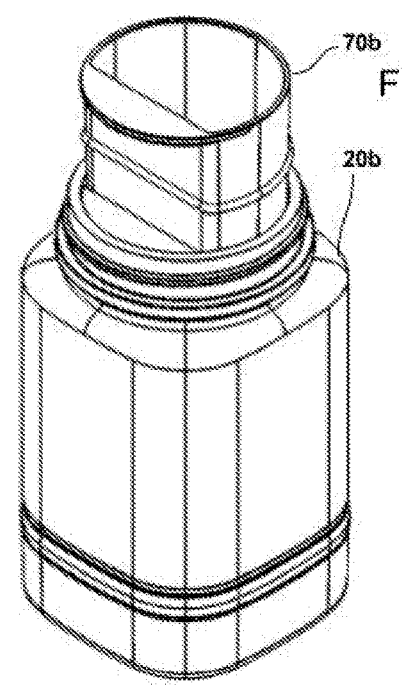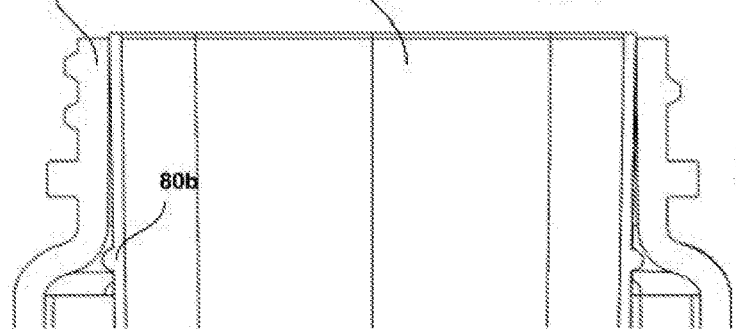

MEDICATION APPARATUS

RELATED APPLICATIONS

The present disclosure is a national stage entry, filed under 35 U.S.C. § 371, of International Application No. PCT/US2017/053888, filed on Sep. 28, 2017, which claims the benefit of and priority to: U.S. Provisional Patent Application No. 62/400,728, entitled "Apparatus and Method for Remote Management of Medication and Medication Packages" and filed on Sep. 28, 2016; U.S. Provisional Patent Application No. 62/407,656, entitled "Apparatus and Methods for Disposable and Reusable Smart Medication Packaging Inserts" and filed on Oct. 13, 2016; and U.S. Provisional Patent Application No. 62/414,261, entitled "Systems and Methods for Closure Detection and Activation of Smart Medication Containers" and filed on Oct. 28, 2016. The contents of the above-referenced patent applications are incorporated by reference herein in their entireties.

TECHNICAL FIELD

The subject matter described herein relates to apparatuses including at least one of a smart medication container, one or more cartridges to be fit within a medication container, and a smart cap to close a medication container. The present disclosure also relates to systems and computer-implemented methods for determining and providing different interventions to patients, caregivers, and/or other parties (e.g., pharmacies) aimed at, for example, improving or maintaining a patient's adherence rate to a medication regimen and/or improving the management of an inventory of medication by the patient, caregiver, and/or other party such as a pharmacy.

BACKGROUND

Medications are packaged in several different types of containers. Conventional medication containers, however, do not safely secure the medication and do not provide easy access of the medication stored therein. Moreover, traditional medication containers do not detect whether or when the medication has been removed from the medication container, much less do so accurately. Conventional medication containers further do not have communication capabilities that enable communication with a remote server computer that can use the communicated data to generate reminders and alerts for a patient. Furthermore, traditional medication containers do not allow removable customized cartridges to be placed therein and thus, for example, such medication containers are wasted after every use.

SUMMARY

The present disclosure relates to apparatuses including at least one of a smart medication container, one or more cartridges to be fit within a medication container, and a smart cap to close a medication container. The smart medication container can advantageously fulfill one or more (e.g., all) of the following objectives: safely secure the medication; allow easy access of the medication in the medication container; detect when medication has been or is likely to have been removed from the medication container; and communicate, via a communication network, the details of detections by the medication container with a remote server computer that can use those details to generate reminders and alerts for a patient and/or other entity or facility such as a pharmacy.

The customized cartridges can be removably inserted (e.g., by a patient or pharmacy representative) in the above-described smart medication container. In some implementations, the smart cap of the smart medication container can activate or cause one or more actions by the smart medication container (e.g., one or more measurements by one or more sensors), and/or signal or detect whether the cap is present on the smart medication container.

In one aspect, a medication container is described. The medication container can include a frame, a drawer, a plurality of slots in the drawer, at least one of a first set of one or more sensors and a second set of one or more sensors, and an electronic transmitter. The drawer can be configured to slide into and out of the frame. The plurality of slots in the drawer can be configured to receive a plurality of cartridges containing medication. The first set of one or more sensors, which can be referred to as one or more drawer sensors, can be configured to detect whether the drawer has moved more than a preset distance into or out of the frame. The second set of one or more sensors, which can be referred to as one or more cartridge sensors, can be configured to detect whether a cartridge of the plurality of cartridges has been removed from or inserted to a corresponding slot of the plurality of slots. The electronic transmitter (e.g., including a network interface) can be configured to transmit to a server computer via a communication network data characterizing, for example, at least one of whether the drawer has moved more than the preset distance into or out of the frame, whether the cartridge has been removed from or inserted into the corresponding slot, and/or timing data associated with these detections, such as time of the detection by the one or more sensors, duration of time a slot has remained vacant, duration of time a slot has remained occupied by a cartridge, duration of time the drawer has remained closed, and/or duration of time the drawer has remained open.

In some variations, one or more of the following can be implemented either individually or in any combination. The server computer can be configured to generate at least one of an alert, reminder, or recommendation based at least in part on the received data. All of the plurality of cartridges can include the same medication. The frame can include one or more hooks. The one or more hooks can allow the frame to be hung and/or the frame to be mateably stacked with another frame. The plurality of slots can be in series. Each slot may include one or more sensors to determine whether a corresponding cartridge has been removed.

The medication container can further include a magnet attached to, for example, the drawer, or alternatively, the frame in a region adjacent to an end of the drawer. The one or more sensors can be configured to detect a movement of the magnet to detect whether the drawer has moved more than the preset distance out of the frame. The magnet can be made of a rare-earth material.

The second set of one or more sensors can be affixed within, for example, the drawer, or alternatively, the frame. The second set of one or more sensors can be one or more weight sensors, infrared sensors, touch sensors or capacitance sensors to detect whether the cartridge has been removed from and/or placed into the corresponding slot. The second set of one or more sensors can be positioned in the frame. The second set of one or more sensors can be configured to detect objects within a preset distance, the second set of one or more sensors detecting the presence or absence of the cartridge. The second set of one or more sensors can be alternatively or additionally configured to detect a quantity of content within one or more cartridges (e.g., quantity of liquid medication or pills, as indicated by weight, fluid ounces, number of pills, or any other suitable quantification metric or combination of such metrics).

In another aspect, another medication container is described. This medication container can include a frame, one or more sensors, and an electronic transmitter. The frame can include a plurality of slots configured to slidably receive (receive in a sliding manner) a plurality of cartridges containing medication. The plurality of cartridges can be configured to slide into and out of the plurality of slots of the frame. The one or more sensors, which can be referred to as one or more cartridge sensors, can be configured to determine whether each slot of the plurality of slots encapsulates, houses, stores, contains or otherwise includes a corresponding cartridge. The electronic transmitter (e.g., including a network interface) can be configured to transmit to a server computer via a communication network data characterizing, for example, whether or not one or more of the slots encapsulates, houses, stores, contains or otherwise includes a cartridge and/or timing data associated with these detections, such as time of the detection by the one or more sensors, duration of time a slot has remained vacant, and/or duration of time a slot has remained occupied by a cartridge.

In some variations, one or more of the following can be implemented. The plurality of slots can include four slots arranged in a two-by-two configuration that has two slots above the other two slots. The one or more sensors can be alternatively or additionally configured to detect a quantity of content within one or more cartridges (e.g., quantity of liquid medication or pills, as indicated by weight, fluid ounces, number of pills, or any other suitable quantification metric or combination of such metrics).

In yet another aspect, an apparatus is described that can include a container and a cartridge. The container can be configured to be closed with a cap. The cartridge can encapsulate, house, store, contain or otherwise include medication configured to be inserted within the container. The cartridge, when completely inserted within the container, can allow the closing of the container with the cap.

In some variations, one or more of the following can be implemented either individually or in any combination. A body of the cartridge can fit within a cavity within the container. A portion of the cartridge can overlie a top of the container in a region where the container accepts the cap. One or more locations on an outer surface of the cartridge can include an adhesive that sticks to an inner surface of the container. A portion of the cartridge can extend externally to the container and can be configured to serve as a grip for holding the container. A portion of the cartridge can extend externally to the container and can be configured to serve as a display element. The display element can be configured to display data identifying content within the cartridge. The display element can include a printed label containing the data identifying content within the cartridge. The display element can have a rectangular shape. Alternately, the display element can have a cylindrical shape. The apparatus can one or more sensors, which can be referred to as one or more cartridge sensors, configured to detect the presence and/or absence of the cartridge and/or a quantity of content within the cartridge (e.g., quantity of liquid medication or pills, as indicated by weight, fluid ounces, number of pills, or any other suitable quantification metric or combination of such metrics). The apparatus can include one or more processors and/or an electronic transmitter (e.g., including a network interface) for communicating sensor data and/or other data with a remote server computer.

The cartridge can be configured to be closed or covered with at least one of a plug and a liner. Each of the plug and the liner can be different and separate from the cap. The cartridge can be configured to be sealed by each of the plug and the liner to prevent content within the cartridge from falling out. Each of the plug and the liner can be removable from the cartridge. The cartridge can include a desiccant chamber and at least one desiccant packet. The desiccant chamber can include perforations that allow moisture to pass from a body of the cartridge into the desiccant packet and to physically separate content of the cartridge from the desiccant packet.

In one aspect, a system (e.g., medication apparatus) is described that can include a container, a container sensor element, a cap, and a cap sensor element. The cap can be configured and used to close the container. The cap sensor element can be affixed to or within the cap. The container sensor element can be in communication with the cap sensor element to detect whether the cap is present within a threshold distance from the container sensor element. In some variations, the container sensor element detects whether the cap sensor element is within a threshold distance. In other variations, the cap sensor element detects whether the container sensor element is within a threshold distance.

In some variations, one or more of the following can be implemented either individually or in any combination. The system can include a pull-tab component configured to be inserted within a battery compartment of the container to prevent the container from drawing power from a battery, and to be removed to allow the container to draw power from the battery. The container sensor element and/or cap sensor element, and/or a different one or more sensors, can be configured to detect a quantity of content within the container (e.g., quantity of liquid medication or pills, as indicated by weight, fluid ounces, number of pills, or any other suitable quantification metric or combination of such metrics).

The system can include electrical circuitry communicatively coupled to the container sensor element and/or the cap sensor element. The electrical circuitry (e.g., one or more processors and a network interface) can be configured to send, via a communication network and to a server computer, data indicating when the cap is open and/or closed, one or more times that the cap is open and/or closed (e.g., as indicated by one or more timestamps generated by the one or more sensors or one or more processors of the medication container), one or more lengths or durations of time the cap remains open and/or closed, and/or the quantity of the content within the container (e.g., the quantity of content within a cavity of the container or a cartridge contained in the cavity of the container).

In one aspect according to some implementations, a server computer can be configured to trigger electronic transmission of, and the electrical circuitry of a medication container and/or user computer can be configured to receive, data indicating an alert (e.g., reminder or recommendation) from the server computer. The server computer can be configured to trigger the alert based at least in part on data received from a medication container. The server can trigger an alert to the medication container and/or other computing device when, for example, the server computer determines: that a quantity of the content in a medication container is below a threshold value (e.g., as determined by comparing data received from one or more sensors of a medication container to a threshold value); that a patient associated with the medication container is likely to have missed a dose or refill of medication or is likely to miss one or more future doses or refills (e.g., as determined by the server computer based at least in part on one or more detections of one or more sensors of the medication container, such as one or more drawer sensors, cartridge sensors, and/or cap or container sensors, and patient medication regimen data stored in one or more databases and accessible to the server computer); and/or that a pharmacy, other entity, or facility that includes the medication container has not or is likely to have not dispensed or refilled medication as expected (e.g., as determined by the server computer based at least in part on one or more detections of the one or more sensors of the medication container, such as one or more drawer sensors, cartridge sensors, and/or cap or container sensors, and dispensation scheduling data stored in one or more databases and accessible to the server computer).

In one aspect according to some implementations, at least one communication receiver of a server computer can be configured to receive data via a first communication network from circuitry on one or more medication containers described herein (e.g., a medication container including one or more cartridges, a drawer, and/or having a cap and/or container sensor). Such data can be, for example, data corresponding to one or more measurements of one or more of the sensors described herein, such as one or more sensor measurements of one or more drawer sensors, cartridge sensors, and/or cap and/or container sensors, timing data associated with the sensor data, and/or data generated by one or more processors of the medication container, for example, based on the detected sensor data. Based at least in part on the receipt of such data, and/or other data (e.g., historical data stored by or otherwise accessible to the server computer in a database), the server computer (e.g., including one or more processors and a network interface) may determine whether at least one criterion is satisfied and based on the determination trigger one or more reminders and/or alerts to a patient, a caregiver, and/or other entity (e.g., a pharmacy). For example, such alerts, which can include text, audio, imagery, video, or any combination thereof, may be transmitted to the medication container(s) themselves and/or to other computing devices.

In some implementations, the at least one communication receiver of server computer can receive data from a medication container over the communication network indicating, for example, that a patient has or is likely to have missed a dose of medication (e.g., when the medication container is within the possession of and configured for use by a patient or caregiver), that medication was, or was not, removed from a medication container or dispensed (e.g., when the medication container is within the possession of and configured for use by a pharmacy, other entity, or facility), and/or that a medication container or one or more cartridges of a medication container were not refilled or are in need of a refill. For example, each time the drawer is moved (e.g., moved at least a threshold distance as determined by the one or more drawer sensors) or at any other suitable time or interval, the medication container can provide data from the one or more drawer sensors and/or other sensors (e.g., cartridge sensors) and/or other data to the server computer. The server computer can interpret that data alone or in combination with other data (e.g., timing data and/or historical data) as indicating when medication has been removed from or added to the container and the server computer can determine based at least in part on such data whether a patient is likely to have missed a dose, whether a pharmacy or other entity or facility has not dispensed a medication as expected, and/or whether a medication container or cartridge in the container is in need of a refill or was not refilled. The server computer can transmit one or more alerts to the medication container and/or to one or more other computing devices based on the determination.

Alternatively or additionally, each time a cartridge is removed from and/or inserted into the medication container (e.g., as determined by the one or more cartridge sensors) or at any other suitable time or interval, the medication container can provide data from the one or more cartridge sensors and/or other sensors (e.g., one or more drawer sensors) and/or other data to the server computer. The server computer can interpret that data alone or in combination with other data (e.g., timing data and/or historical data) as indicating when medication has been removed from or added to the container and the server computer can determine based at least in part on such data whether a patient is likely to have missed a dose, whether a pharmacy or other entity or facility has not dispensed a medication as expected, and/or whether a medication container or cartridge in the container is in need of a refill or was not refilled. The server computer can transmit one or more alerts to the medication container and/or to one or more other computing devices based on the determination.

Alternatively or additionally to the implementations disclosed above, each time a cap is removed from and/or placed on a medication container (e.g., as determined by the one or more cap and/or container sensors) or at any other suitable time or interval, the medication container can provide data from one or more sensors (e.g., one or more cartridge sensors and/or the one or more cap and/or container sensors cap) and/or other data to the server computer. The server computer can interpret that data alone or in combination with other data (e.g., timing data and/or historical data) as indicating when medication has been removed from or added to the container (e.g., based on when a cartridge has been inserted to or removed from the container and/or when the cap is removed) and the server computer can determine based at least in part on such data whether a patient is likely to have missed a dose, whether a pharmacy or other entity or facility has not dispensed a medication as expected, and/or whether a medication container or cartridge in the container is in need of a refill or was not refilled. The server computer can transmit one or more alerts to the medication container and/or to one or more other computing devices based on the determination.

In some implementations, the server computer can receive data over the communication network indicating, for example, alone or in combination with other data: that a preset amount of content within the one or more cartridges or containers was not withdrawn within a preset amount of time and/or was withdrawn after the preset amount of time; that a cartridge or cavity of a medication container was refilled after a preset amount of time; and/or that one or more cartridges of a medication container were not refilled and/or were not removed within a preset amount of time. Such data can be, for example, data corresponding to one or more measurements (e.g., detection events) of one or more of the medication container sensors described herein and received by the server computer from the medication container (e.g., one or more cartridge sensors, one or more drawer sensors, and/or one or more container and/or cap sensors of a medication container). At least one database can be communicatively coupled to the at least one communication receiver. The at least one database can be configured to store at least the received data from the medication container and/or other data (e.g., a medication regimen for a patient, an expected dispensing schedule for a pharmacy or other entity or facility, and/or an expected refill schedule for a medication container or cartridge contained within the medication container). At least one processor can be communicatively coupled to at least one of the at least one communication receiver and the at least one database. The at least one processor can be programmed or otherwise configured or adapted to determine, upon or subsequent to the receipt of the data, whether at least one criterion is satisfied, the at least one processor generating an alert (e.g., reminder) when the at least one criterion is satisfied. At least one communication transmitter can be communicatively coupled to the at least one processor. The at least one communication transmitter can be configured to transmit, via a second communication network, the alert to the medication container and/or one or more other computing devices.

In some variations, one or more of the following can be implemented either individually or in any combination. The server computer is configured to determine that a patient has not adhered to a medication regimen, that a pharmacy or other entity or facility has not adhered to an expected medication dispensation schedule, and/or that a medication container or cartridge within a medication container has not been refilled according to an expected schedule based at least in part on the server computer not receiving a communication from the medication container within a preset amount of time. For example, the server computer can trigger an alert (e.g., reminder) to the medication container and/or another one or more computing devices based at least in part on the server computer identifying that the one or more drawer sensors, one or more cartridge sensors, and/or one or more container and/or cap sensors of a medication container have not been activated within a period of time that exceeds a preset amount of time. The preset amount of time can be set or identified by the server computer based at least in part on data stored in a database and accessible to the server computer indicating: a medication regimen for a patient that identifies an expected frequency of the patient taking a dose; an expected dispensation schedule for a pharmacy or other entity or facility identifying how frequently medication is expected to be dispensed; and/or an expected refill schedule for the medication container or a cartridge contained within the medication container. The server computer can compare this data, for example, to data indicating the last time the server computer received a communication from the one or more sensors of the medication container to determine if the preset amount of time has lapsed without the server computer receiving a further one or more communications from one or more sensors of the medication container. Based at least in part on (e.g., based solely on) the determination, the server computer can trigger one or more alerts to the medication container and/or another one or more computing devices. The computing device can be one of a desktop computer, a laptop computer, a tablet computer, a phablet computer, and a cellular phone. In one implementation, the computing device can be configured to be operated by a patient using the medication container. In another implementation, the computing device can be configured to be operated by at least one of: a caregiver (e.g., hospital, clinician, doctor, nurse, technician, clinical staff member, and/or any other caregiver) treating a patient using the medication container, a pharmacy authorized to provide medication to the patient, and a healthcare company authorized to obtain healthcare data of the patient. In one implementation, the first communication network can be same or substantially the same as the second communication network (e.g., internet). In an alternate implementation, the first communication network can be different and separate from the second communication network. The first communication network can be one or more of a local area network, a wide area network, internet, intranet, Bluetooth network, infrared network, any other network, and any combination thereof. The second communication network can be one or more of a local area network, a wide area network, internet, intranet, Bluetooth network, infrared network, any other network, and any combination thereof.

In one implementation, the satisfying of the at least one criterion can be the server computer determining whether a risk level of a user exceeds a threshold value or otherwise meets, or does not meet, one or more criteria. The at least one programmable processor of the server computer can compute the risk level based at least in part on historical data stored in the database. The historical data analyzed for by the server computer to make the determination can include one or more of: data regarding opening and/or closing of a cap of a medication container (e.g., as provided by one or more of the container and/or cap sensors of the medication container); data regarding sliding in and/or out of a drawer of a medication container (e.g., as provided by one or more drawer sensors of the medication container); data regarding insertion of one or more cartridges into a medication container (e.g., a slot of a medication container) and/or removal of the one or more cartridges from the medication container (e.g., as provided by one or more cartridge sensors of the medication container); an adherence score characterizing a likelihood of adherence of a patient to a medication regimen, which is based at least in part on, for example, past adherence of the patient to the same or a different medication regimen (e.g., a calculated value or score reflecting a patient's past adherence to a medication regimen, such as the fraction or percentage of days the patient has or is likely to have consumed medication on the days the patient was supposed to consume medication as per the medication regimen, where in some variations the server computer calculating the value or score can specifically exclude from the calculation of the score, or alternatively treat differently in the calculation of the score, days of the medication regimen for which a patient was not supposed to consume medication, and where the server can compare the calculated value or score to a threshold value or score to identify whether the patient is high-risk for non-adherence to either directly trigger one or more alerts or to consider by the server computer together with one or more additional criteria in order to determine whether to trigger one or more alerts); a pattern of withdrawing medication from the medication container; the complexity of such a pattern of withdrawing medication (e.g., complexity as determined by the server computer performing a comparison of actual data regarding withdrawal of medication by a user to an expected patient or other entity expected regimen stored in a database accessible to the server computer); a pattern of refilling the medication container or cartridge within a medication container; the inaccuracy of such a pattern of refilling the medication container or a cartridge within the medication container (e.g., inaccuracy as determined by the server computer by comparing actual data regarding one or more refills or a failure to obtain one or more refills to an expected refill schedule stored in a database accessible to the server computer); a type of medication in the medication container; a dosage requirement for consuming the medication; timing of one or more prior communications between the circuitry of the medication container and the at least one communication receiver; data exchanged between the circuitry of the medication container and the at least one communication receiver during the one or more prior communications; and one or more errors noted with respect to the one or more prior communications.

In some variations, the server computer can trigger an alert based on (e.g., based solely on) determining that a medication dose was missed or determining that medication was not dispensed (e.g., by a pharmacy) as expected. In another implementation, the server computer can trigger an alert based on (e.g., based solely on) determining that a medication container (e.g., bottle) was not refilled according to an expected schedule. In another implementation, the server computer can trigger an alert based on (e.g., based solely on) receiving a message from a user (e.g., patient, caregiver, or pharmacist) associated with a medication container indicating that additional care is required. In another implementation, the server computer can trigger an alert based on (e.g., based solely on) receiving any other message from a user (e.g., patient, caregiver, or pharmacist) associated with a medication container (e.g., any message at all regardless of content of the message). The server computer can provide different, specialized alerts to a medication container and/or one or more other computers under different circumstances.

In some variations, the server computer can trigger an alert based, at least in part, on both determining that a medication dose was missed and evaluating one or more additional criteria. In one implementation, the additional criterion can be the server computer determining that a user of the bottle (e.g., patient) is high-risk as determined by the server computer based on at least in part one or more data points from previous analysis and/or data stored by the server computer (e.g., an overall adherence score for a patient; a complex dosage pattern as indicated by, for example, sensor data from one or more sensors of a medication container and/or a medication regimen for a patient; inaccurate dosing or refill patterns as indicated by, for example, sensor data from one or more sensors of a medication container and/or a medication regimen for a patient; medication information; previous messaging to the system; and/or other factor(s)). In another implementation, the additional criterion can be the server computer determining that one or more recent doses was also missed (e.g., the server computer determining that one or more recent doses was missed based at least in part on: data stored in a database indicating lack of access to a medication container or cartridge of the medication container within at least one other, prior preset amount of time as indicated by prior sensor data received from the medication container and/or a lack of prior sensor data received from the medication container; and/or data stored in a database indicating lack of withdrawal of a preset amount or quantity of content from a medication container or cartridge in the medication container within at least one other, prior preset amount of time as indicated by prior sensor data received from the medication container). In another implementation, the additional criterion can be the server computer determining that a user or entity is late starting or restarting a planned medication and/or refill cycle (e.g., the server computer determining that the user or entity is late based at least in part on: data stored in a database indicating access to a medication container or cartridge of the medication container after a present amount of time as indicated by sensor data received from the medication container; and/or data stored in a database indicating withdrawal of a preset amount or quantity of content from a medication container or cartridge in the medication container after a present amount of time as indicated by sensor data received from the medication container). In various implementations, the server computer only triggers an alert to a medication container or other computing device when the server computer determines both that a medication dose was missed and the at least one additional criteria is satisfied. The server computer can provide different, specialized alerts to a medication container and/or one or more other computers under different circumstances.

The alert, as described herein, can be data that activates an alarm, which can be audio, visual (e.g., text, imagery, and or video), or both. In various implementations, the alert can be one or more of: a text message, a voice message, a video message, a social media message, an email, a web pop-up, a pager message, any other message, and any combination thereof. The alert can be a reminder in some implementations. The alert can be provided to a medication container and/or to one or more other computing devices.

The details of one or more variations of the subject matter described herein are set forth in the accompanying drawings and the description below. Other features and advantages of the subject matter described herein will be apparent from the description, the drawings, and the claims.

DESCRIPTION OF DRAWINGS

FIGS. 1A, 1B, 2A, 2B, 3, 4A, 4B, 5, 6A, and 6B illustrate some implementations of a smart medication container according to some implementations of the current subject matter.

FIGS. 7A-7C, 8A, 8B, 9A-9C, 10A, 10B, 11A-11C, 12A-12C, 13A-13C, 14A, 14B, and 15-15C illustrate some implementations of removable cartridges within a medication container according to some implementations of the current subject matter.

Like reference symbols in the various drawings indicate like elements.

DETAILED DESCRIPTION

Figure 3:
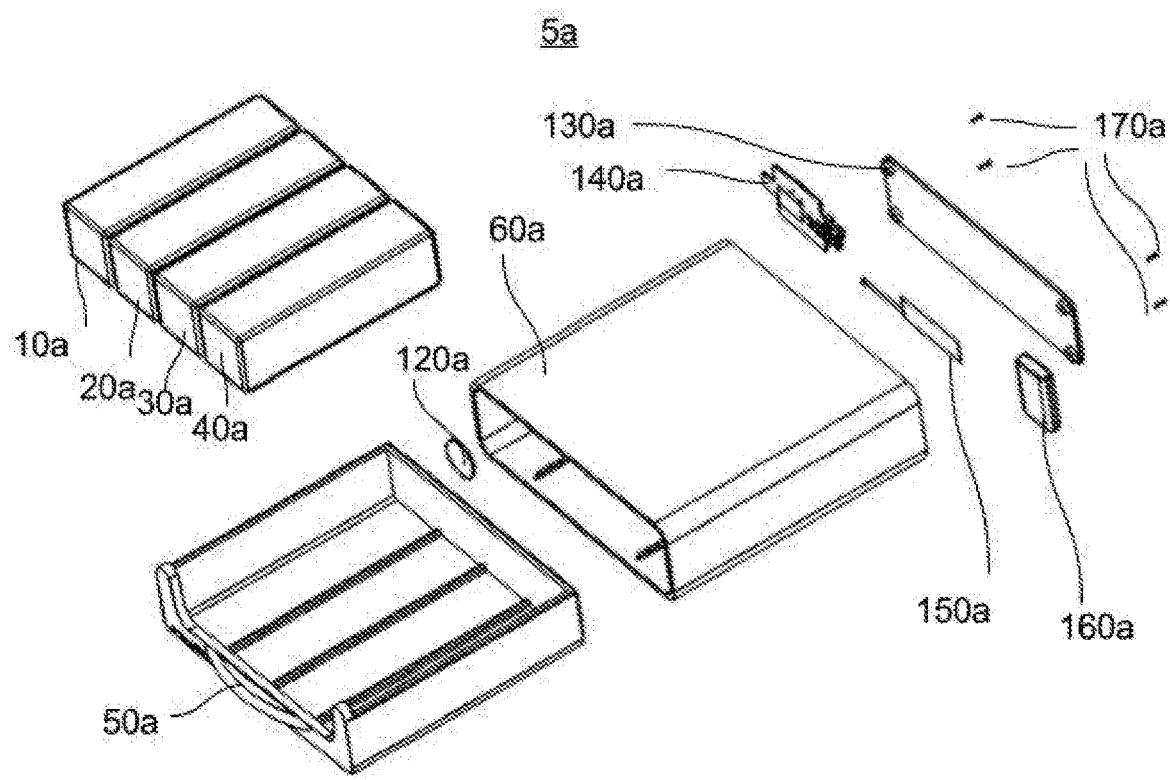

FIGS. 1A, 1B, 2A, 2B, 3, 4A, 4B, 5, 6A, and 6B illustrate some implementations of a smart medication container according to some implementations of the current subject matter.

FIG. 1A illustrates a first implementation of a medication container 5a. The medication container 5a can include multiple (e.g., four) cartridges 10a, 20a, 30a and 40a, a drawer 50a, and a frame 60a. The four cartridges 10a, 20a, 30a and 40a can be removably, or alternately permanently, inserted into and lifted out (e.g., entirely or partially) of the drawer 50a, which can slide within the frame 60a. The medication container 5a can determine when the drawer 50a is being slid in or out of the frame 60a. In some implementations, the medication container 5a can determine whether any of cartridges 10a, 20a, 30a and 40a are being removed and/or inserted. The frame 60a can include guides and rails on the inside, which can guide the drawer 50a to enable straight and linear motion of the drawer 50a. In some implementations, each of cartridges 10a, 20a, 30a and 40a can be or can include one or more containers of medication, such as bottles (e.g., pill bottles), vials, liquid medication containers, tubes, pouches, boxes, doses, blister packs, spray containers, and/or inhalers. In some implementations, each of cartridges 10a, 20a, 30a and 40a can be or include one or more syringes. In some implementations, each of the cartridges 10a, 20a, 30a and 40a can be a cardboard and/or plastic box having a generally parallelepiped shape (e.g., parallel or almost parallel sides) and that contains the above one or more containers of medication and/or syringe(s).

In various illustrative implementations, each of the four cartridges 10a, 20a, 30a and 40a can be made of one or more of the following materials: cardboard, plastic, glass, and metal. The drawer 50a can be made of one or more of the following materials: plastic and metal. Making the drawer 50a with plastic and/or metal can advantageously minimize friction while opening and closing the drawer 50a, and thus also maximizing durability of the drawer 50a. The frame 60a can be made of one or more of the following materials: plastic and metal (e.g., the same or different material(s) used for drawer 50a).

In various illustrative implementations, medication container 5a can have the following dimensions or range(s) of dimensions. Frame 60a can have a generally parallelepiped body (e.g., parallel or almost parallel sides), which can have rounded corners. Frame 60a can have a generally open face (e.g., face that is open or almost open) for receipt of drawer 50a containing the one or more cartridges 10a, 20a, 30a and 40a. In some implementations, the remaining faces of frame 60a can be fully or substantially closed. In some implementations, frame 60a can be about 8-10 inches wide in a direction perpendicular or generally perpendicular (e.g., at ninety degrees, or almost ninety degrees such as between eighty degrees and one hundred degrees) to a direction of motion of drawer 50a into and out of frame 60a, about 10-14 inches in length (depth), and about 2-4 inches in height.

Drawer 50a in some implementations can have a shape configured to fit through an open face of frame 60a and reside within an open cavity of frame 60a. As described above, drawer 50a can contain one or more rails or recesses (e.g., on bottom and/or side surfaces of drawer 50a) for mated connection to one or more recesses or rails, respectively, of frame 60a. Drawer 50a can have a generally (e.g., fully or substantially fully) open top face for receipt of the one or more cartridges 10a, 20a, 30a and 40a. Drawer 50a can have a partially open front face. As shown, for example, in FIG. 1A, this can include a drawer lip or ridge that allows for retention of the cartridges 10a, 20a, 30a and 40a and prevents them from unintentionally falling out of medication container 5a. It can also simultaneously allow an observer to visually identify the presence, or absence, of the one or more cartridges 10a, 20a, 30a and 40a within medication container 5a and optionally the ability to read, for example, information printed or otherwise shown on cartridges 10a, 20a, 30a and 40a. In some implementations, drawer 50a can be about 8-10 inches wide in a direction perpendicular or generally perpendicular (e.g., at ninety degrees, or almost ninety degrees such as between eighty degrees and one hundred degrees) to a direction of motion of drawer 50a into and out of frame 60a, about 10-14 inches in length (depth), and about 2-4 inches in height. For example, in some implementations, the length, width, and height of drawer 50a can be selected to be slightly less than that of frame 60a to enable a snug friction fit of drawer 50a within frame 60a and to prevent the entire apparatus from unnecessarily consuming space.

Each of cartridges 10a, 20a, 30a and 40a in some implementations can have a shape configured to fit within an open area of drawer 50a. Stated another way, drawer 50a can be configured such that its open area is sized and configured for receipt (e.g., mating receipt to establish a friction fit) of the cartridges 10a, 20a, 30a and 40a. In some implementations, when the multiple cartridges are inserted within drawer 50a, and the drawer 50a is inserted within the frame 60a, the cartridges can collectively occupy all or substantially all of the open space within the interior of the frame 60a, for example, with the exception of one or more walls or ridges that separate different cartridge components of drawer 50a. Such physical separators are shown, for example, in FIG. 3. In some implementations, each of cartridges 10a, 20a, 30a and 40a can be about 1-4 inches (e.g., 1-3 inches) in width, about or less than 6-14 inches (e.g., 6-10 inches) in length (depth), and about or less than 1-4 inches (e.g., 1-3 inches) in height.

FIG. 1B illustrates a second implementation of a medication container 65a according to some implementations of the current subject matter. The medication container 65a can include multiple (e.g., four) cartridges 10a, 20a, 30a and 40a, and a frame 70a. The four cartridges 10a, 20a, 30a and 40a can be removably, or alternately permanently, inserted into the frame 70a. Each of the four cartridges 10a, 20a, 30a and 40a can be individually slid into and out of the frame 70a. The medication container 65a can determine when a cartridge 10a, 20a, 30a or 40a is slid into or out of the frame 70a. The frame 70a can optionally include guides and rails on the inside, which can correspondingly guide each cartridge 10a, 20a, 30a and 40a in a straight and linear motion. For example, each cartridge can contain one or more rails or recesses (e.g., on bottom and/or side surfaces of the cartridge) for mated connection to one or more recesses or rails, respectively, of frame 70a. In other implementations, only the frame 70a, but not the cartridge(s), can contain guides or rails. Each of cartridges 10a, 20a, 30a and 40a can be removed by sliding that cartridge individually out of the corresponding slot. A front face of container 65a can include one or more ridges or tabs at one or more (e.g., all) of the front, generally open faces of the slots to prevent corresponding one or more cartridges from falling out of the slots. The cartridge(s) can be lifted over the tab(s) or ridge(s) before being slid back into the slots and then retained in the slots by the tab(s) or ridge(s) once the trailing end of the cartridge(s) clear the tab(s) or ridge(s).

In various illustrative implementations, medication container 65a can have the following form factor and dimensions or range(s) of dimensions. Frame 70a can have a parallelepiped or a generally parallelepiped body (e.g., body with parallel or almost parallel sides), which can have rounded corners. Frame 70a can have a face defining a plurality (e.g., four) open regions or cavities for receipt of one or more cartridges 10a, 20a, 30a and 40a. In some implementations, the remaining faces of frame 70a can be fully or substantially closed. In some implementations, frame 70a can be about 5-8 inches wide in a direction perpendicular or generally perpendicular (e.g., at ninety degrees, or almost ninety degrees such as between eighty degrees and one hundred degrees) to a direction of motion of the cartridges 10a, 20a, 30a or 40a into and out of frame 70a, about 10-14 inches in length, and about 5-8 inches in height.

Each of cartridges 10a, 20a, 30a and 40a in some implementations can have a shape configured to fit within an open area of frame 70a. Stated another way, frame 70a can be configured such that it has multiple open areas or cavities and such areas are sized and configured for receipt (e.g., mating receipt to establish a friction fit) of the cartridges 10a, 20a, 30a and 40a. In some implementations, when the multiple cartridges are inserted within frame 70a, the cartridges can collectively occupy all or substantially all of the open space within the interior of the frame 70a. In some implementations, each of cartridges 10a, 20a, 30a and 40a can be about 1-4 inches (e.g., 1-3 inches) in width in a direction perpendicular or generally perpendicular (e.g., at ninety degrees, or almost ninety degrees such as between eighty degrees and one hundred degrees) to a direction of motion of that cartridge into and out of frame 70a, about 6-14 inches (e.g., 6-10 inches) in length, and about 1-4 inches (e.g., 1-3 inches) in height.

The medication containers 5a and 65a can be configured to lay flat on a surface (e.g., a shelf) that can support the bottom of those medication containers. For the medication container 5a, the surface of the frame 60a adjacent to the bottom surface of the drawer 50a can be configured to rest on the shelf. Such configuration can provide stability to the medication containers 5a and 65a.

FIG. 2A illustrates a medication container 75a, in which the drawer 50a can slide into and out of the frame 80a, which includes hooks 90a that allow: (1) the medication container 75a to be hung (e.g., from a shelf such as in a refrigerator), and/or (2) the medication container 75a to be stacked with another medication container 75a. Two medication containers 75a can be stacked for purposes of physically storing the medication containers 75a to minimize storage space. Such stacking can involve in some implementations matingly connecting hooks 90a located at the top or bottom of one medication container 75a to corresponding features (e.g., loops or recesses) in the bottom or top, respectively, of another medication container (e.g., another container 75a). The container 75a can be the same as or similar to container 5a (FIG. 1A) in all other respects.

FIG. 2B illustrates a medication container 95a, in which the cartridges 10a, 20a, 30a and 40a can individually slide into and out of the frame 100a, which includes hooks 110a that allow: (1) the medication container 95a to be hung (e.g., from a shelf such as in a refrigerator), and/or (2) the medication container 95a to be stacked with another medication container 95a. Two medication containers 95a can be stacked for purposes of physically storing the medication containers 95a to minimize storage space. Such stacking can involve in some implementations matingly connecting hooks 110a located at the top or bottom of one medication container 95a to corresponding features (e.g., loops or recesses) in the bottom or top, respectively, of another medication container (e.g., another container 95a). The container 95a can be the same as or similar to container 65a (FIG. 1B) in all other respects.

FIG. 3 illustrates an exploded view showing various components of the medication container 5a of FIG. 1A. The medication container 5a can include, in addition to the components discussed above, a magnet 120a, a wireless circuit board embedded with various components such as a sensor 140a (e.g., a switch such as a reed switch to detect whether the magnet 120a has moved), a wireless antenna 150a, a battery 160a, a back-plate 130a, and four fasteners 170a.

The magnet 120a can be either attached to or placed adjacent to the drawer 50a. When the magnet 120a movably translates within the frame 60a, the sensor 140a can detect whether the magnet 12 has moved, thereby indicating whether the drawer 50a has slid into or out of the frame 60a. The wireless circuit board can include in some implementations, in addition to the sensor 140a, other electronic components such as a microprocessor, a wireless module, radio-frequency (RF) circuitry, power circuitry, and one or more integrated sensors. This microprocessor can transmit, via the wireless antenna 150a and to a server computer via a communication network, the data indicating whether the drawer 50a has slid into or out of the frame 60a and/or other data (e.g., other data produced by other sensor(s) described by the present disclosure, such as one or more cartridge sensors described below in connection with FIGS. 5, 6A and 6B). The communication network can be one or more of a local area network, a wide area network, internet, intranet, Bluetooth network, infrared network, any other network, and any combination thereof. The battery 160a can supply power to the entire medication container 5a. The battery can be integrally installed within the frame 60a. The back-plate 130a can secure all of the electronic components, using four fasteners 170a. Systems and methods for enabling a device to communicate information including sensor data to a server via a communication network are described in U.S. Pat. No. 8,754,769, which is hereby incorporated by reference herein in its entirety.

The magnet 120a can be made from rare-earth materials, such as neodymium. While neodymium is described, in alternate implementations the magnet 120a can be made of other rare-earth materials, such as one or more of samarium cobalt, neodymium, any alloy of rare-earth elements (e.g., elements in the lanthanide series, plus scandium and yttrium), other rare-earth materials, and any combination thereof. Using rare-earth materials for the magnet 120a makes the magnet a strong permanent magnet, which can cause the magnet to have and maintain for a long time (e.g., many years) a strong magnetic field, which advantageously does not need its own power source for at least that time.

FIG. 4A illustrates electronic components of the medication container 5a when the drawer 50a is in an extended (fully or partially extended) configuration. The electronic components can include a magnet 120a, a wireless circuit board embedded with, fixed to, or adjacent to various components such as a back-plate 130a, and a sensor 140a to detect movement of drawer 50a by determining whether the magnet 120a has moved. In the extended configuration, the distance 180a between the magnet 120a and the back-plate 130a can be, for example, the maximum possible or alternatively less than the maximum possible but the distance at which sensor 140a detects and registers a change in the status in movement of the drawer 50a. In some implementations, the sensor 140a may not register a movement of drawer 50a so long as the magnet 120a has moved less than the distance 180a. The distance 180a in some implementations can be, for example, 0.25 inches, or within the range of 0.125 inches to 5 inches. In an alternate implementation, the sensor 140a can be configured to detect whether the magnet 120a has moved as long as the magnet 120a is within another preset the distance from the magnet 120a, wherein the preset distance can be less than the distance 180a. In another alternate implementation, this preset distance can be more than or equal to the distance 180a.

FIG. 4B illustrates some electronic components of the medication container 5a when the drawer 50a is in a fully retracted configuration. The drawer can be extended to achieve the extended configuration of FIG. 4A.

Figure 5:
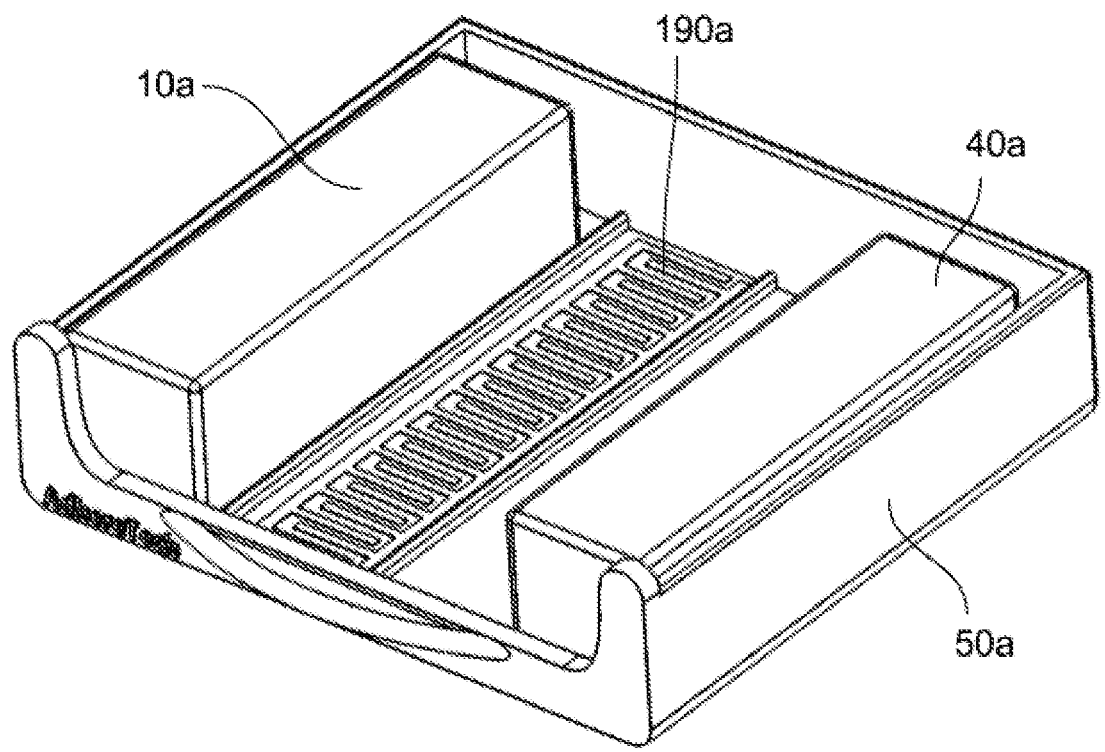

FIG. 5 illustrates another implementation of a sensor 190a within the medication container 5a. The sensor 190a can be a cartridge sensor that detects the presence of, or absence of, a cartridge within the medication container 5a. In some implementations, the medication container 5a can include a separate sensor 190*a* for each cartridge 10*a*, 20*a*, 30*a* and 40*a*, in which case each sensor 190*a* can detect the presence of, or absence of, each corresponding cartridge. In some implementations, alternatively or additionally the sensor 190*a* detecting the presence or absence of a cartridge in the medication container 5*a*, the sensor 190*a* can detect an amount of content (e.g., weight, number of pills, or quantity of liquid medication) within the cartridge 10*a*, 20*a*, 30*a* or 40*a*. In the implementation shown in FIG. 5, sensor 190*a* can include a plurality of (e.g., two or more) electrodes (e.g., metal electrodes) in an interleaved, interdigitated pattern. The electrodes of the sensor 190*a* can be generally flat (e.g., flat or almost flat) and generally contained within a two-dimensional plane. The electrodes can span the entire or substantially the entire compartment in which the corresponding cartridge is to be received. In other implementations, the electrodes can span only a portion (e.g., approximately three-quarters, approximately half, or less) of the compartment in which the corresponding cartridge is to be received. In some implementations, one or more sensor(s) that are the same as or similar to sensor 190*a* can be included in one or more (e.g., all) of the slots of the medication container 65*a* (FIG. 1B), for example, on or within a bottom (e.g., floor) portion of the slots do determine whether one or more cartridge(s) 10*a*, 20*a*, 30*a* and 40*a* are present and/or the amount of content of the medication in one or more of the cartridge(s) 10*a*, 20*a*, 30*a* and 40*a*.

In various implementations, each sensor 190*a* can determine whether one or more cartridge(s) 10*a*, 20*a*, 30*a* or 40*a* are present within drawer 50*a* and/or the content of the medication container 5*a* or any cartridge 10*a*, 20*a*, 30*a* or 40*a* (e.g., weight, number of pills, or quantity of liquid medication) via touch, capacitance, weight, light, visual queue, or any other manner. For example, each sensor 190*a* can be a capacitance sensor or a touch sensor. The sensor 190*a* can be embedded onto or otherwise affixed to the drawer 50*a*. Each sensor 190*a* can be connected (e.g., via a wired connection) or otherwise in communication with (e.g., via a wireless connection) the wireless circuit board, providing the wireless circuit board data about presence, absence, and/or contents of the cartridges 10*a*, 20*a*, 30*a* and/or 40*a*. In some implementations, the connection between one or more sensors 190*a* and the circuit board may be by way of a flexible cable (e.g., ribbon wire). In some implementations, the connection between one or more sensors 190*a* and the circuit board may be by way of a metal contact (e.g., rail or strip) that is electrically connected to the sensor 190*a* and is partially exposed on an exterior portion of the drawer 50*a* and that, when the drawer 50*a* is inserted into the frame 60*a*, makes electrical contact with a corresponding metal contact that is electrically connected to the circuit board and that is exposed on a portion of the frame 60*a*.

In one example, each sensor 190*a* can be a binary capacitance based touch sensor, which can be configured to detect the presence and/or absence of a single cartridge 10*a*, 20*a*, 30*a* or 40*a* in a corresponding slot for that cartridge. In this example, a contact between the cartridge 10*a*, 20*a*, 30*a* or 40*a* and the sensor 190*a* yields a change in capacitance of the sensor 190*a*, which the sensor 190*a* can translate into a binary detection of that cartridge being installed or removed from the medication container 5*a*. The wireless circuit board that includes or otherwise communicates with the sensor 190*a* can further include a capacitance-to-digital converter integrated circuit that can measure and indicate the capacitance and, in some implementations, compare it to a threshold to determine if the measured capacitance is indicative of a cartridge being present or absent. The medication container 5*a* can include an array of sensors 190*a*, which can detect installation or removal of an array of cartridges 10*a*, 20*a*, 30*a* and 40*a*.

Figure 6A:
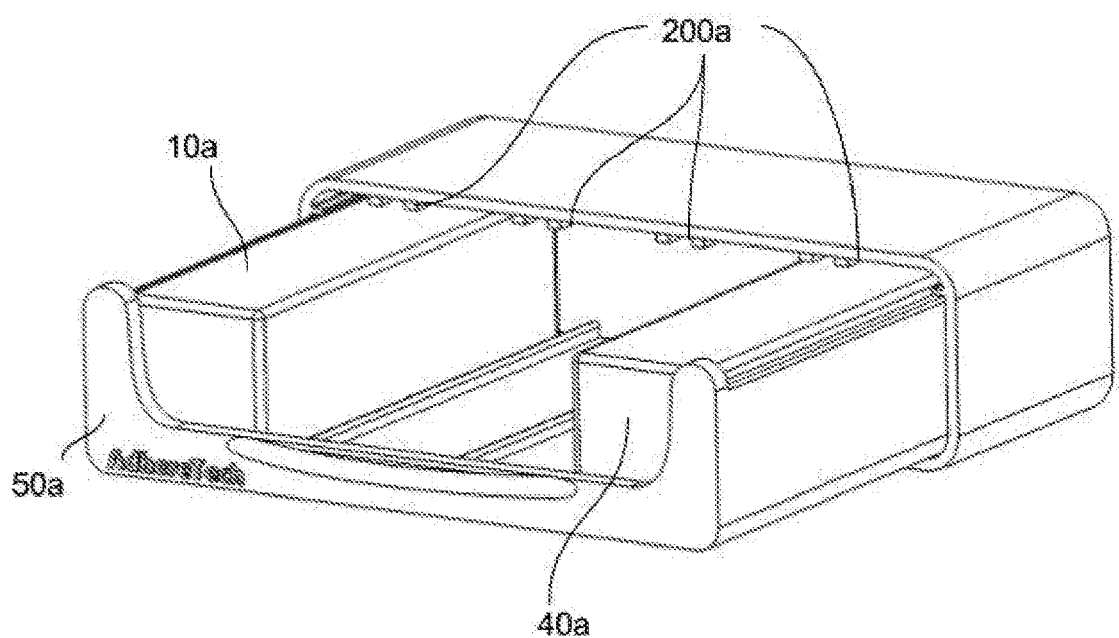
Figure 6B:
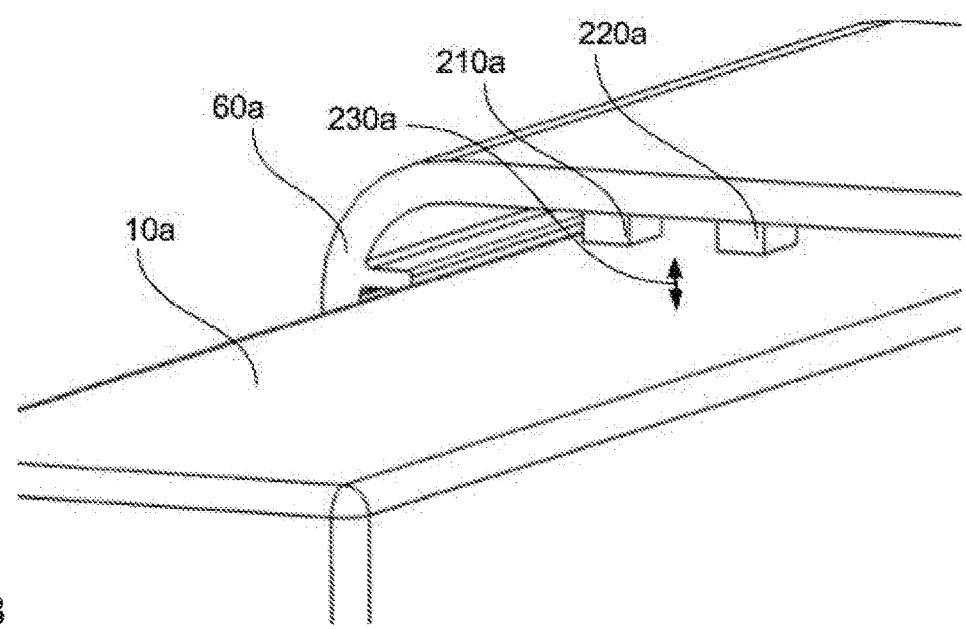
Figure 6C:
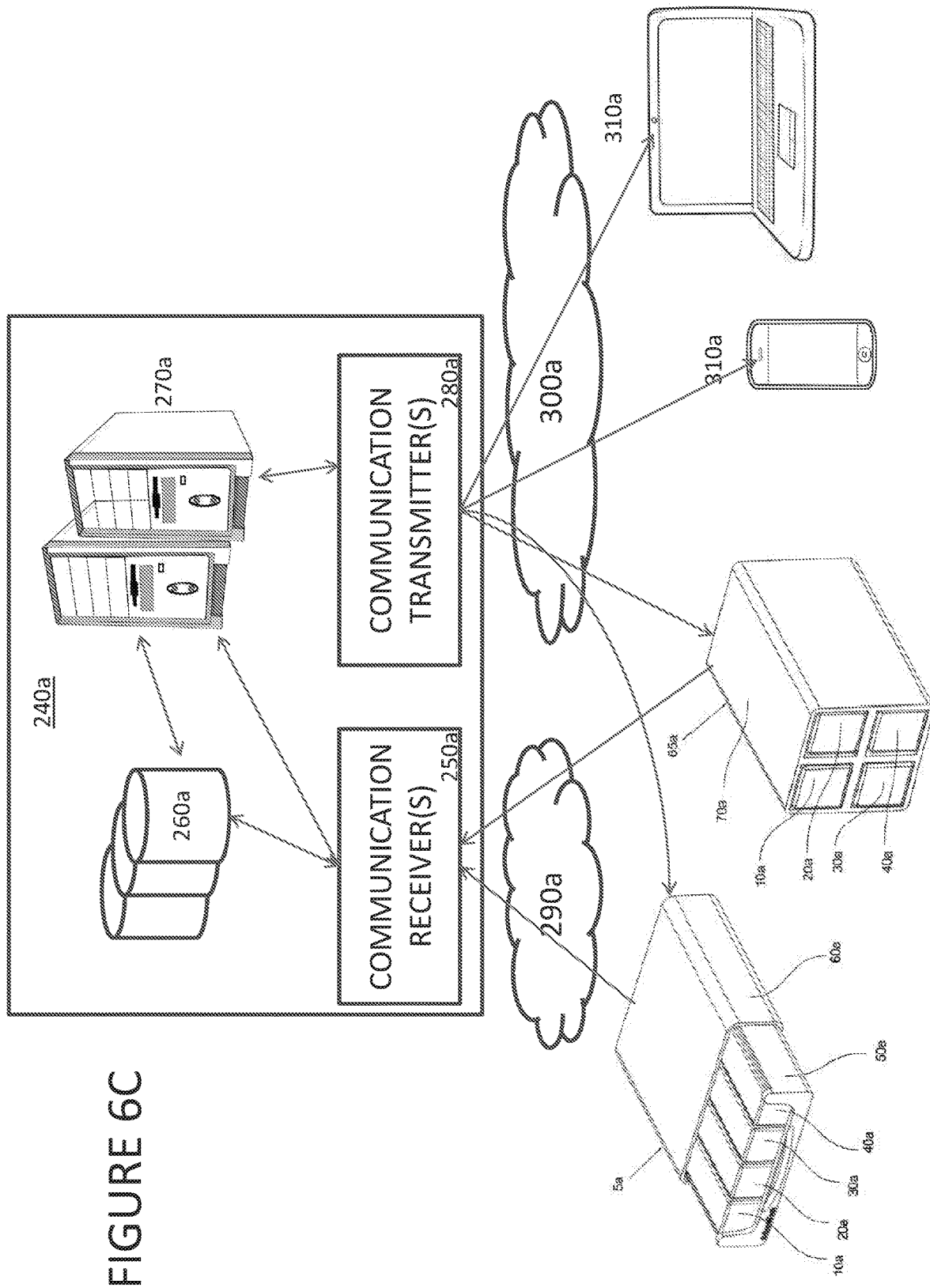
FIG. 6C illustrates a server computer that can communicate with circuitry on a medication container to generate reminders and/or alerts for a patient, a caregiver, a pharmacy, any other individual or entity, and/or any combination thereof.

The wireless circuit board can communicate, via a communication network, the details of the detections by the one or more sensors and/or processing of the same by one or more processors of the circuit board of the medication container with a remote server computer that can use those details, for example, to generate one or more reminders and alerts for a patient, caregiver, and/or other party (e.g., a pharmacy), as shown for example in FIG. 6C. The communication network can be one or more of a local area network, a wide area network, internet, intranet, Bluetooth network, infrared network, any other network, and any combination thereof. In various implementations, the wireless circuit board can be affixed to or housed by the frame of the medication container (e.g., frame 60*a* or 70*a*). In various implementations, the wireless circuit board can be affixed to or housed by the drawer (e.g., drawer 50*a*).

FIG. 6A illustrates a plurality of infrared distance sensors 200*a* each configured to detect the presence or absence of a cartridge 10*a*, 20*a*, 30*a* or 40*a* in a slot corresponding to that cartridge.

FIG. 6B illustrates components of the sensor 200*a*. The sensor 200*a* can be embedded onto, affixed to, or at least partially integrated with or housed by the frame 60*a*. The sensor 200*a* can include a transmitter 210*a* and a receiver 220*a*. The sensor 200*a* can be an infrared sensor, which can detect interference between the transmitter 210*a* and the receiver 220*a*. Such detection can indicate whether the corresponding cartridge 10*a*, 20*a*, 30*a* or 40*a* is installed or removed within a threshold distance 230*a*. The threshold distance 230*a* can represent the range of distance within which the presence of a cartridge 10*a*, 20*a*, 30*a* or 40*a* can be detected. That is, the cartridge 10*a*, 20*a*, 30*a* or 40*a* is detected if it is within the threshold distance 230*a*. The sensor can transmit or electronically provide data characterizing the detection to the circuit board of medication container 5*a*. The sensor can communicate via a wired or wireless connection with the circuit board. An array of sensors 200*a* can be used to detect an array of cartridges 10*a*, 20*a*, 30*a* or 40*a*.

The wireless circuit board can communicate, via a communication network, the details of the detections by the one or more sensors 200*a* and/or processing of the same by one or more processors of the circuit board of the medication container with a server computer that can use those details to generate one or more reminders and alerts for a patient, caregiver, and/or other party (e.g., a pharmacy), as shown for example in FIG. 6C. The server computer can be remote to the wireless circuit board, such as in a different room within a same building, a different building, a different city, a different state, a different country, or any remote distance. The communication network can be one or more of a local area network, a wide area network, internet, intranet, Bluetooth network, infrared network, any other network, and any combination thereof.

FIG. 6C illustrates a server computer 240*a* that can communicate with the circuitry on a medication container (e.g., medication container 5*a*, 65*a*, 75*a* or 95*a*) to generate one or more reminders and/or alerts for a patient, a caregiver, a pharmacy, any other individual or entity, and/or any combination thereof. The server computer 240*a* can include at least one communication receiver 250*a*, at least one database 260*a*, at least one programmable processor 270*a*, and at least one communication transmitter 280*a*. The at least one programmable processor 270a can be, in different implementations, a processor, a microprocessor, a controller, a microcontroller, a data processor, a programmable data processor, and/or the like. In various implementations, the server computer 240a may be in two-way communication with the medication container and/or one or more other computers (e.g., one or more computers 310a).

In various implementations, the at least one communication receiver 250a of the server computer 240a can be configured to receive data via the first communication network 290a from circuitry on one or more medication containers described herein (e.g., a medication container 5a, 65a, 75a or 95a containing one or more cartridges 10a, 20a, 30a, and 40a). Such data can be, for example, data corresponding to one or more measurements (e.g., binary detections) of one or more of the sensors described herein, such as: one or more sensor measurements indicating opening and/or closing of a drawer of a medication container (e.g., sliding in or out of the drawer 50a) and/or timing data (e.g., via a timestamp) indicating a time of such opening and/or closing as identified by the one or more sensors or the one or more processors of the medication container; one or more sensor measurements indicating whether one or more cartridges (e.g., 10a, 20a, 30a, and 40a) is present within one or more slots of a medication container (e.g., one or more measurement(s) indicating whether cartridges have been inserted to and/or removed from the medication container) and/or timing data (e.g., via a timestamp) indicating a time of such insertion and/or removal the cartridge(s) as identified by the one or more sensors or the one or more processors of the medication container; and/or one or more sensor measurements indicating a quantity of medication within a medication container or one or more cartridges (e.g., cartridges 10a, 20a, 30a, and 40a of a medication container) and/or timing data (e.g., via a timestamp) indicating a time of such measurements as identified by the one or more sensors or the one or more processors of the medication container. Based at least in part on the receipt of such data, and/or other data (e.g., historical data stored by or otherwise accessible to the server computer in a database 260a, such as data indicating one or more previous measurements received by the one or more sensors and/or timing data regarding timing of such measurements), the server computer including one or more processors 270a can determine whether at least one criterion is satisfied and based on the determination trigger one or more reminders and/or alerts to a patient, a caregiver, and/or other entity (e.g., a pharmacy). For example, such alerts, which can include text, audio, imagery, video, or any combination thereof, can be transmitted to the medication container(s) themselves (e.g., medication containers 5a, 65a, 75a or 95a) and/or to other computing devices (e.g., computing devices 310a).

In some implementations, the communication network can receive data from a medication container (e.g., medication container 5a, 65a, 75a, and/or 95a) indicating that one or more of the medication containers 5a, 65a, 75a and/or 95a is in need of a refill of medication (e.g., when medication container 5a, 65a, 75a and/or 95a is used to dispense medication at a pharmacy or other facility). In some implementations, the communication network can receive data from a medication container (e.g., medication container 5a or 65a) indicating that a patient has or is likely to have missed a dose of medication (e.g., when medication container 5a, 65a, 75a and/or 95a is utilized for a particular patient).

In one aspect, the at least one communication receiver 250a can be configured to receive, via a first communication network 290a and from circuitry on a medication container 5a, 65a, 75a or 95a, data indicating that a preset amount of content within the one or more cartridges 10a, 20a, 30a or 40a was not withdrawn within a preset amount of time. For example, this data can indicate whether the cartridges themselves are present and/or have been removed (e.g., a binary detection), as determined, for example, by one or more sensors configured to detect the presence or absence of one or more of the cartridges. Alternatively or additionally, this data can identify one or more specific amounts or quantities of contents with one or more cartridges (e.g., weight or quantity of liquid medication or pills), as determined, for example, by the one or more sensors configured to determine a weight or quantity within one or more cartridges. The at least one database 260a can be communicatively coupled to the at least one communication receiver 250a. The at least one database 260a can be configured to store at least the received data. The at least one programmable processor 270a can be communicatively coupled to at least one of (e.g., both of) the at least one communication receiver 250a and the at least one database 260a. The at least one programmable processor 270a can determine, upon or subsequent to the receiving of the data, whether at least one criterion is satisfied, the at least one programmable processor 270a generating an alert when the at least one criterion is satisfied. The at least one communication transmitter 280a can be communicatively coupled to the at least one programmable processor 270a. The at least one communication transmitter 280a can be configured to transmit, via a second communication network 300a, one or more alerts to a computing device 310a (e.g., a pharmacy computer) and/or the medication container (e.g., medication container 5a, 65a, 75a or 95a).

The indication that the preset amount of content within the one or more cartridges 10a, 20a, 30a or 40a was not withdrawn can indicate that a dose of medication contained within the medication container 5a, 65a, 75a or 95a was missed or otherwise not removed or dispensed within the preset amount of time. Each computing device 310a is one of a desktop computer, a laptop computer, a tablet computer, a phablet computer, and a cellular phone. In one implementation, the computing device 310a can be configured to be operated by a patient using the medication container 5a, 65a, 75a or 95a. In another implementation, the computing device 310a can be configured to be operated by at least one of: a caregiver (e.g., hospital, clinician, doctor, nurse, technician, clinical staff member, and/or any other caregiver) treating a patient using the medication container 5a, 65a, 75a or 95a, a pharmacy authorized to provide medication to one or more patients, and a healthcare company authorized to obtain healthcare data of one or more patients. In one implementation, the first communication network 290a can be same or substantially the same as the second communication network 300a (e.g., internet). In an alternate implementation, the first communication network 290a can be different and separate from the second communication network 300a. The first communication network 290a can be one or more of a local area network, a wide area network, internet, intranet, Bluetooth network, infrared network, any other network, and any combination thereof. The second communication network 300a can be one or more of a local area network, a wide area network, internet, intranet, Bluetooth network, infrared network, any other network, and any combination thereof.

In one implementation, the satisfying of the at least one criterion can be a risk level of a user such as a patient or other entity (e.g., pharmacy) exceeding a threshold value.

For example, the at least one processor 270a can determine an estimated risk for a user (e.g., patient) or entity (e.g., pharmacy) and determine that the estimated risk exceeds a defined level of risk that the patient will not adhere to a medication regimen, or that a pharmacy or other entity will not dispense medication as expected. The at least one programmable processor 270a can compute the risk level based on at least in part historical data stored in the database 260a. For example, the historical data used by the at least one processor 270a to compute the risk level can include one or more of: an adherence score characterizing a likelihood of adherence of a patient to a medication regimen or a pharmacy or other entity following an expected dispensing schedule, a pattern of withdrawing medication from the medication container 5a, 65a, 75a or 95a, a pattern of refilling the medication container 5a, 65a, 75a or 95a (e.g., with one or more cartridges as detected by one or more cartridge sensors), a type of medication in the medication container 5a, 65a, 75a or 95a, data indicative of expected removal of medication by a user, pharmacy or other entity, one or more dosage requirements for consuming the medication, timing of one or more prior communications between the circuitry of the medication container and the at least one communication receiver 250a, data exchanged between the circuitry of the medication container and the at least one communication receiver 250a during the one or more prior communications, and one or more errors noted with respect to the one or more prior communications.

The at least one processor 270a of a server computer according to various implementations can determine an adherence score characterizing a likelihood of adherence of a patient to a medication regimen. For example, the adherence score can be based at least in part on past adherence of the patient to the same or a different medication regimen. The adherence score can be a calculated value or score reflecting a patient's past adherence to a medication regimen, such as the fraction or percentage of days the patient has or is likely to have consumed medication on the days the patient was supposed to consume medication as per the patient's medication regimen ("on" days), where in some variations the server computer calculating the value or score can specifically exclude from the calculation of the score, or alternatively treat differently in the calculation of the score, days of the medication regimen for which a patient was not supposed to consume medication ("off" days). For example, for some medications, the medication regimen will require a patient to take the medication for a preset number of "on" days (e.g., 21 days) followed by another preset number of "off" days for which the patient is not supposed to consume the medication (e.g., 7 days). The at least one database 260a can store data regarding such a medication regimen for a patient, or any other medication regimen containing any other pattern or instructions regarding "on" and/or "off" days, and the at least one processor 270a of a server computer can exclude or consider differently such "off" days when calculating an adherence score for the patient. For example, if the at least one processor 270a of the server computer in the above example accesses data indicating that the patient consumed medication on 18 of the 21 "on" days and none of the 7 "off" days, the patient's adherence score can be 18/21 or 0.857 (i.e., the off days can be ignored). If the threshold for high-risk patient is 0.90 or less, the at least one processor 270a of the server computer can identify the patient as a high risk patient by determining that the patient's statistic of 0.857 is less than 0.90. As another example, if the at least one processor 270a of the server computer accesses data indicating that the patient consumed medication on 21 of the 21 "on" days (i.e., the patient took medication on every day the patient was supposed to) but also consumed the medication on 6 of the 7 "off" days (i.e., non-adherence for 6 of the 7 off days), the patient's adherence score can be 22/28 or 0.785 (i.e., taking medication on "off" days counts negatively against the patient). If the threshold for high-risk patient is 0.90 or less, the at least one processor 270a of the server computer can identify the patient as a high risk patient by determining that the 0.785 is less than 0.90. In still another example, if the at least one processor 270a of the server computer accesses data indicating that the patient consumed medication on 21 of the 21 "on" days (i.e., the patient took medication on every day the patient was supposed to) but also consumed the medication on 3 of the 7 "off" days (i.e., non-adherence for 3 of the 7 "off" days), the patient's adherence score can be 26.5/28 or 0.946 (i.e., reflecting that the system discounts non-adherence on "off" days by 50%, i.e., 3 non-adherent "off" days equals 1.5 missed days when calculating the patient's score). If the threshold for high-risk patient is 0.90 or less, the at least one processor 270a of the server computer can identify the patient as a low risk patient by determining that the 0.946 is greater than 0.90. In the above example, without the discount for "off" days, the patient's adherence score could alternatively be 25/28 or 0.892 and the at least one processor 270a of the server computer could identify the patient as a high risk patient by determining that the 0.892 is less than 0.90. The at least one processor 270a of the server computer can compare the calculated value or score for a patient to a threshold value or score to identify whether the patient is high-risk for non-adherence to directly trigger one or more alerts to a medication container and/or to another one or more computers. In some variations, the at least one processor 270a of the server computer can consider the patient's value or score and the threshold value or score together with one or more additional criteria in order to determine whether to trigger one or more alerts to a medication container and/or to another one or more computers. In some variations, the at least one processor 270a of the server computer can determine an adherence score for a pharmacy or other entity in a like manner as described above by comparing data regarding an expected medication dispensation schedule for the pharmacy or other entity to actual data regarding medication dispensation by the pharmacy or other entity.

In another implementation, the satisfying of the at least one criterion can be determined by data indicative of lack of withdrawal of the preset amount of content within the one or more cartridges 10a, 20a, 30a or 40a within another preset amount of time (e.g., a prior time period, which can indicate a pattern of missed doses or failure to dispense medication). In some implementations, this data can be historical data that is used alone or in combination with other historical data identified above to determine a risk level for a user such as a patient or other entity such as a pharmacy. The lack of withdrawal of the preset amount within the other preset amount of time can indicate that a dose or other removal of medication contained within the medication container 5a, 65a, 75a or 95a was missed within the other preset amount of time. The data indicating the lack of withdrawal of the preset amount within the other preset amount of time can be stored in the database 260a. The at least one programmable processor 270a can determine the lack of withdrawal of the preset amount within the other preset amount of time by receiving from the database 260a the data indicating the lack of withdrawal of the preset amount within the other preset amount of time.

In yet another implementation, the satisfying of the at least one criterion can be the withdrawal of the preset amount of content within the one or more cartridges 10a, 20a, 30a or 40a after the preset amount of time. The withdrawal of the preset amount of content within the one or more cartridges 10a, 20a, 30a or 40a after the preset amount of time can indicate that a patient took the medication late or that it was dispensed late by a pharmacy or other entity. The at least one programmable processor 270a can be configured to receive, from the circuitry on the medication container 5a, 65a, 75a or 95a, data indicating withdrawal of the preset amount of content within the one or more cartridges 10a, 20a, 30a or 40a. The at least one programmable processor 270a can identify a time of the receiving of the data indicating the withdrawal (e.g., as indicated by timing data received from the medication container or generated locally by the at least one processor 270a or other circuitry of the server computer) to determine whether the withdrawal is after the preset amount of time.

In another implementation, the satisfying of the at least one criterion can be a refilling of at least one cartridge of the one or more cartridges 10a, 20a, 30a or 40a after a preset amount of time. The refilling of the at least one cartridge after the preset amount of time can indicate that the refilling of the at least one cartridge was late. The at least one programmable processor 270a can be configured to receive, from the circuitry on the medication container 5a, 65a, 75a or 95a, data indicating the refilling of the at least one cartridge (e.g., data generated by one or more cartridge sensors of the medication container). The at least one programmable processor 270a can identify or determine a time of the refilling of the at least one cartridge to determine whether the refilling was late.

The alert, as described herein, can be data that activates an alarm, which can be audio, visual, or both. In various implementations, the alert can be one or more of: a text message, a voice message, a video message, a social media message, an email, a web pop-up, a pager message, any other message, and any combination thereof. The alert can be a reminder in some implementations.

In another aspect, the at least one communication receiver 250a can be configured to receive, via a first communication network 290a and from circuitry on a medication container 5a, 65a, 75a or 95a, data indicating that one or more cartridges 10a, 20a, 30a or 40a of a medication container 5a, 65a, 75a or 95a were not refilled within a preset amount of time. The at least one programmable processor 270a can be configured to generate an alert upon the receiving of the data. The at least one communication transmitter 280a can be configured to transmit, via a second communication network 300a, the alert to a computing device 310a and/or the medication container itself.

In some implementations, the at least one processor 270a is configured to determine that a medication container or cartridge within a medication container has not been refilled according to an expected schedule based at least in part on the at least one processor 270a not receiving a communication from the medication container within a preset amount of time. For example, the at least one processor 270a can trigger an alert (e.g., reminder) to the medication container and/or another one or more computing devices 310a based at least in part on the at least one processor 270a identifying that the one or more drawer sensors and/or one or more cartridge sensors of the medication container have not been activated within a period of time that exceeds a preset amount of time. The preset amount of time can be set or identified by the at least one processor 270a based at least in part on data stored in database 260a and accessible to the at least one processor 270a indicating one or more of: a medication regimen for a patient that identifies an expected frequency of the patient taking a dose; an expected dispensation schedule for a pharmacy or other entity or facility identifying how frequently medication is expected to be dispensed; and/or an expected refill schedule for the medication container or a cartridge contained within the medication container. The at least one processor 270a can compare this data, for example, to data indicating the last time the at least one processor 270a received a communication from the one or more sensors of the medication container to determine if the preset amount of time has lapsed without at least one processor 270a receiving a further one or more communications from one or more sensors of the medication container. Based at least in part on (e.g., based solely on) the determination, the at least one processor 270a can trigger one or more alerts to the medication container and/or another one or more computing devices 310a.

In one implementation, the computing device 310a can be configured to be operated by a patient. In another implementation, the computing device 310a can be configured to be operated by at least one of: a caregiver treating the patient, a pharmacy authorized to provide medication to the patient, and a healthcare company authorized to obtain healthcare data of the patient.

In another aspect, the at least one communication receiver 250a can be configured to receive a message (e.g., text message or response to a graphical prompt on the medication device itself or on a webpage) from a first computing device 310a and/or the medication container itself via a first communication network 290a. The at least one programmable processor 270a can generate an alert upon the receiving of the message. The at least one communication transmitter 280a can be configured to transmit, via a second communication network 300a, the alert to a second computing device 310a.

The first computing device 310a can be configured to be operated by a patient. The second computing device 310a can be configured to be operated by at least one of: a caregiver treating the patient, a pharmacy authorized to provide medication to the patient, and a healthcare company authorized to obtain healthcare data of the patient. In one implementation, the message can include a request for additional care.

FIGS. 7A-7C, 8A, 8B, 9A-9C, 10A, 10B, 11A-11C, 12A-12C, 13A-13C, 14A, 14B, and 15-15C illustrate some implementations of removable cartridges within a medication container (e.g., bottle) according to some implementations of the current subject matter.

FIG. 7A illustrates a removable cartridge 10b configured to be inserted into a smart medication container 20b. The cartridge 10b can be installed vertically into the medication container 20b. In some implementations, the cartridge 10b can be fitted tightly within the medication container 20b while allowing the original cap of the medication container 20b to still be used without any modification to the cap. The cartridge 10b is configured to be easily installed and removed by a user, such as a patient. The cartridge 10b can be configured to store any type of medication, such as one or more of tablets, capsules, powder, and liquid. In some implementations, the cartridge 10b can have a height that is equal to or approximately equal to the height of medication container 20b. In some implementations the cartridge 10b can have a height that is less than the height of medication container 20b, but more than half the height of medication container 20b. In some implementations, the length and width of cartridge 10b (in directions perpendicular or substantially perpendicular to the height of cartridge 10b) can be less than the length and width of medication container 20b, but more than half the length and width of medication container 20b within a body portion of medication container 20b. In one implementation, the cartridge 10b can have dimensions of 1.75 inches×3 inches×1.75 inches, and in other implementations the cartridge can be within the ranges of about 1 to 3 inches wide, about 2 to 7 inches high, and about 1 to 3 inches in length.

FIG. 7B illustrates that the outer shape of the cartridge 10b can conform to the inner shape of the medication container 20b. In some implementations, the cartridge 10b can be made of plastics such as low-density polyethylene (LDPE), high-density polyethylene (HDPE), polypropylene (PP), other plastics, any other materials, and/or any combination thereof. The cartridge 10b can be fabricated by injection molding, blow molding, thermoforming, and/or any other method. In some implementations, the cartridge 10b can include an adhesive at one or more specific locations on the outer surface of the cartridge 10b for permanent installation of the cartridge 10b within the medication container 20b.

The cartridge 10b can advantageously serve in some implementations as a wall-thickener for the smart medication container 20b, thereby enabling an increased: resistance to chemicals, resistance to permeability of moisture, resistance to oxygen permeability, and rigidity of the structure. In some implementations, the cartridge 10b can have a portion that extends out from the body of the medication container 20b to serve as a handle or grip, which can allow a user to insert and remove the medication container 20b as needed.

FIG. 7C illustrates the position where the cartridge 10b has been fully inserted into the medication container 20b. FIG. 7C illustrates a position wherein the cartridge 10b is partially removed from the medication container 20b. FIG. 7A illustrates a position in which the cartridge 10b is fully removed from the medication container 20b.

In some implementations, the medication container 20b can be a bottle. The medication container 20b can have a generally cylindrical (e.g., cylindrical or almost cylindrical) or jar-like shape. The medication container 20b can include a body portion and a top portion for receipt of a cap. Medication container 20b can have a width and length of approximately 2.37 inches in its body portion. The height of the medication container 20b along both its body portion can be approximately 3.4 inches, and the height of the top portion (which is the portion with threads that enable the medication container 20b to be closed with a cap) can be approximately 0.6 inches. As shown, the top portion can have threading or at least one ridge for receipt of a correspondingly threaded or configured cap (e.g., a twist-on or snap-fit cap). In other implementations, the medication container can have a width in a body portion of about 1 to 4 inches, a length in a body portion of about 1 to 4 inches, and a height of about 3 to 6 inches.

Figure 8A:
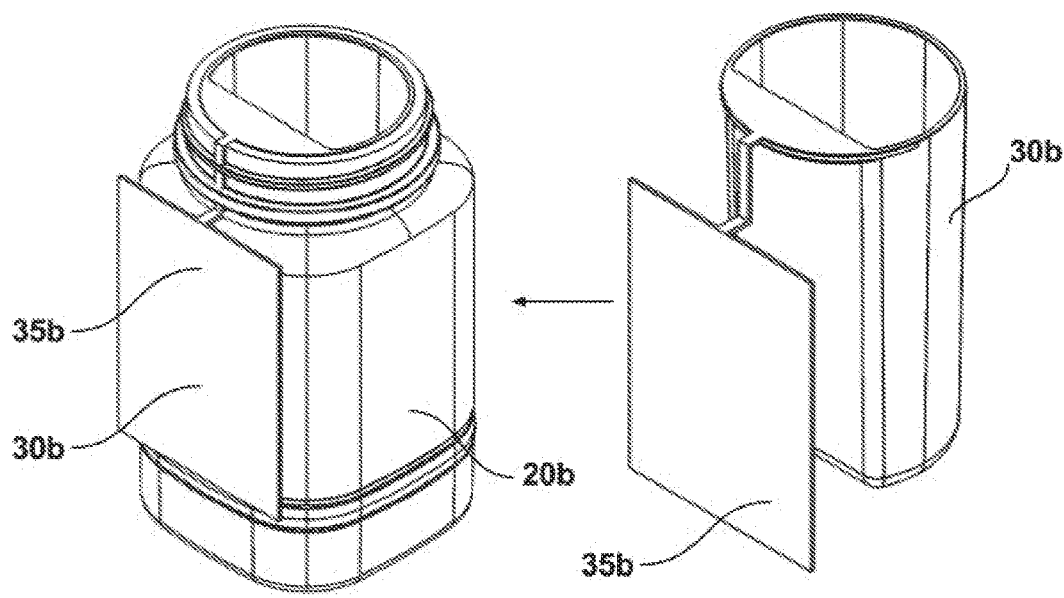

FIG. 8A illustrates a first implementation of another cartridge 30b that is configured to be removably inserted (that is, can be removed after insertion) into the smart medication container 20b. A single flat wing 35b can be a part of the cartridge 30b. The flat wing 35b can display information about the medication contained within the medication container 20b and/or function as a handle. The flat wing 35b can be rectangular-shaped or square-shaped. The flat wing 35b can have a width and length that is less than or equal to the width and length of the medication container 20b. The cartridge 30b can be fitted tightly within the medication container 20b while allowing the original cap of the medication container 20b to still be used without any modification to the cap. As shown, the flat wing 35b can be connected by a thin and low-profile tab to a portion of the cartridge 30b that is intended to reside within an interior cavity medication container 20b. The thin tab can include a first elbow joint at or near the top of the cartridge 30b and another elbow joint at or near the location where a body portion of the medication container 20b meets a top portion of the medication container 20b that is configured for receipt of a cap. The cartridge 30b can be configured to be easily installed and removed by a user, such as a patient. The cartridge 30b can be configured to store any type of medication, such as one or more of tablets, capsules, powder, and liquid.

The cartridge 30b can be made of plastics such as low-density polyethylene (LDPE), high-density polyethylene (HDPE), polypropylene (PP), other plastics, any other materials, and/or any combination thereof. The cartridge 30b can be fabricated by injection molding, blow molding, thermoforming, and/or any other method. In some implementations, the cartridge 30b can include an adhesive at one or more specific locations on the outer surface of the cartridge 30b for permanent installation of the cartridge 30b within the medication container 20b. The cartridge 30b can be fabricated by thermoforming, die-cutting, extrusion, any other method, or any combination thereof.

The medication information can be applied on the flat wing 35b via direct screen printing, thermal transfer, label application, any other method, or any combination thereof.

Figure 8B:
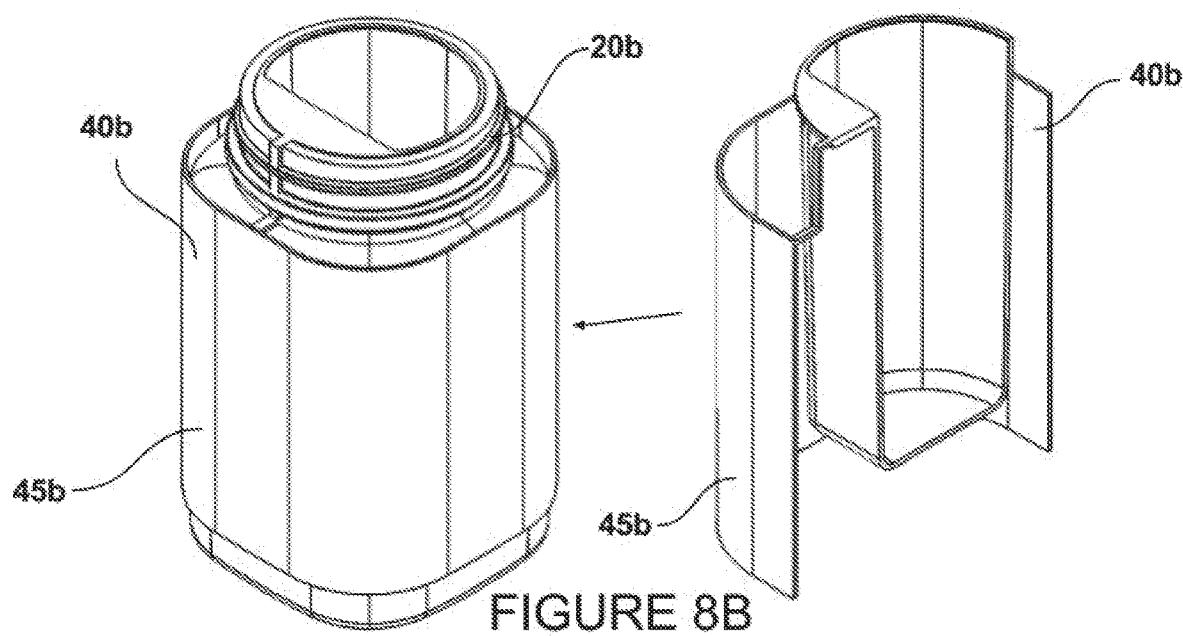

FIG. 8B illustrates another implementation of a cartridge 40b that is configured to be removably inserted (that is, can be removed after insertion) into the smart medication container 20b. A round or generally round and continuous wing 45b can be a part of the cartridge 40b. This wing 45b can surround the entire medication container 20b from all sides in some implementations. In an alternate implementation according to some implementations, the round wing 45b can partially cover the medication container 20b. The round wing 45b can display information about the medication contained within the medication container 20b. The cartridge 40b can be fitted tightly within the medication container 40b while allowing the original cap of the medication container 20b to still be used without any modification to the cap. The cartridge 40b can be configured to be easily installed and removed by a user, such as a patient. The cartridge 40b can be configured to store any type of medication, such as one or more of tablets, capsules, powder, and liquid. In some implementations, other elements of cartridge 40b as shown can be similar to the elements of cartridge 30b describes above.

The cartridge 40b can be made of plastics such as low-density polyethylene (LDPE), high-density polyethylene (HDPE), polypropylene (PP), other plastics, any other materials, and/or any combination thereof. The cartridge 40b can be fabricated by injection molding, blow molding, thermoforming, and/or any other method. In some implementations, the cartridge 40b can include an adhesive at specific locations on the outer surface of the cartridge 40b for permanent installation of the cartridge 40b within the medication container 20b. The cartridge 40b can be fabricated by thermoforming, die-cutting, extrusion, any other method, or any combination thereof.

The medication information can be applied on the round wing 45b via direct screen printing, thermal transfer, label application, any other method, or any combination thereof.

Figure 9A:
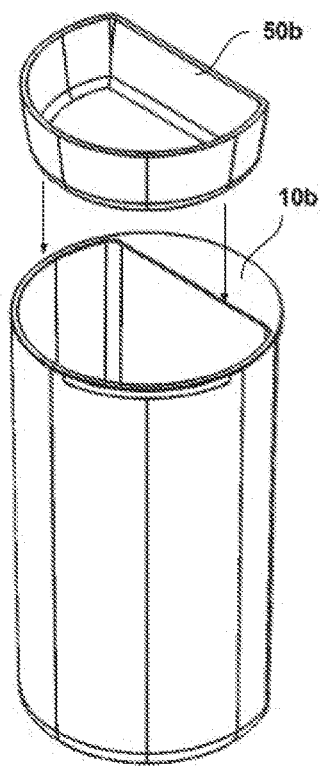

FIG. 9A illustrates a plug 50*b* that can be inserted onto the cartridge 10*b* to seal or close the cartridge 10*b*. The sealing or closing of the cartridge 10*b* can prevent the falling out of the contents within the cartridge 10*b*. The plug 50*b* can include features, such as a flap or tab, that can enable a removal of the plug 50*b* from the cartridge 10*b* by a user. The plug 50*b* can need to be removed in order to refill the contents of the cartridge 10*b*. The plug 50*b* can thus enable the cartridge 10*b* to act as a stand-alone container for medication. The plug 50*b* can also provide space for placing a label identifying the contents within the cartridge 10*b*. The plug 50*b* can be made of same or similar material(s) as that forming the cartridge 10*b*. In some implementations, the same or a similar plug 50*b* can be provided on cartridges 30*b* and 40*b*.

Figure 9B:
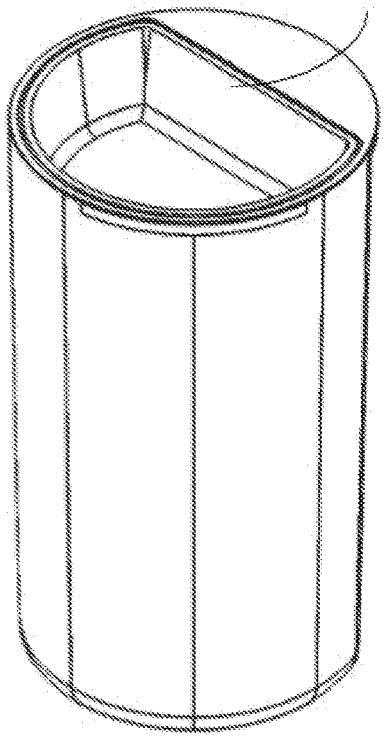

FIG. 9B illustrates the cartridge 10*b* that has been closed or sealed with the plug 50*b*.

Figure 9C:
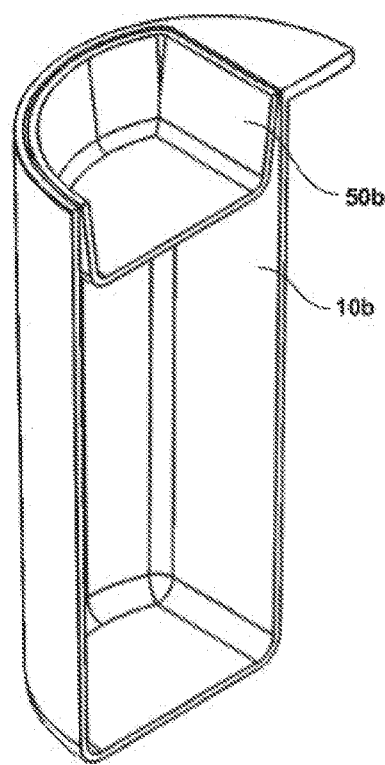

FIG. 9C illustrates a vertical cross-section of the cartridge 10*b* that has been closed or sealed with the plug 50*b*.

Figure 10A:
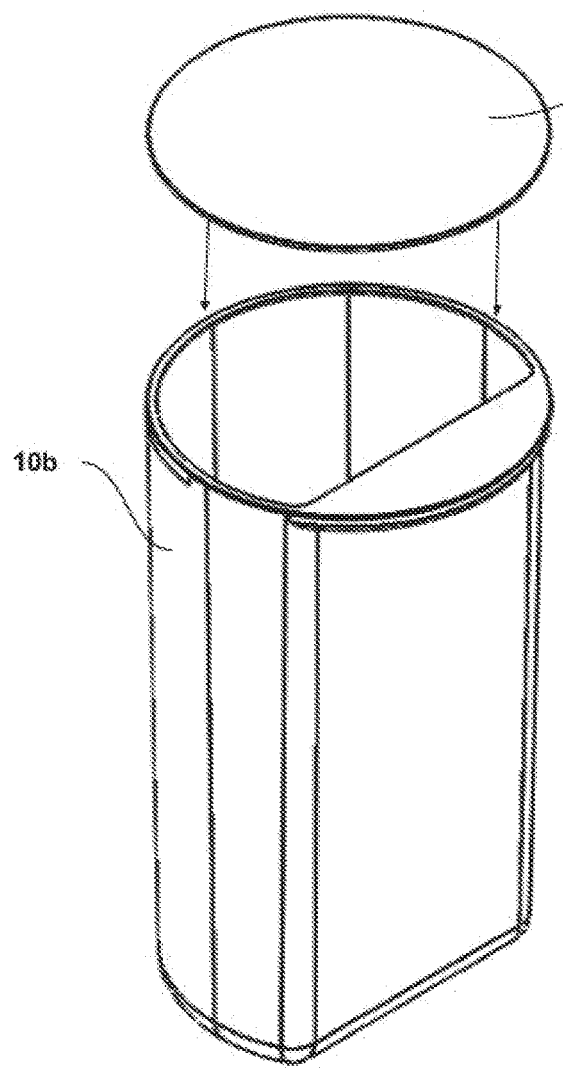

FIG. 10A illustrates a liner 60*b* that can be attached to the top of the cartridge 10*b* via an induction sealing mechanism. The liner 60*b* can also be referred to as an induction liner. While induction sealing mechanism is described for attaching the liner 60*b* to the top of the cartridge 10*b*, in alternate implementations other attachment mechanisms can be used, such as one or more of gluing, nailing, stitching, or any other attachment mechanism or combination thereof. The sealing or closing of the cartridge 10*b* can prevent the falling out of the contents within the cartridge 10*b*. The liner 60*b* can include features, such as a flap or tab, that can enable a removal of the liner 60*b* from the cartridge 10*b* by a user. The liner 60*b* can need to be removed in order to refill the contents of the cartridge 110*b*. The liner 60*b* can thus enable the cartridge 10*b* to act as a stand-alone container for medication. The liner 60*b* can also provide space for placing a label identifying the contents within the cartridge 10*b*. The liner 60*b* can be made of same or similar material(s) as that forming the cartridge 110*b* in some implementations. In some implementations, the liner 60*b* can be made of one or more of foam, paper, aluminum, or any other material or combination thereof. In some implementations, liner 60*b* can have a thickness that is about 0.035 inch. In other implementations, the liner 60*b* can have a thickness of 0.02 inches to about 0.05 inches, or about 0.01 inches to about 0.2 inches. In some implementations, the same or a similar liner 60*b* can be provided on cartridges 30*b* and 40*b*.

Figure 10B:
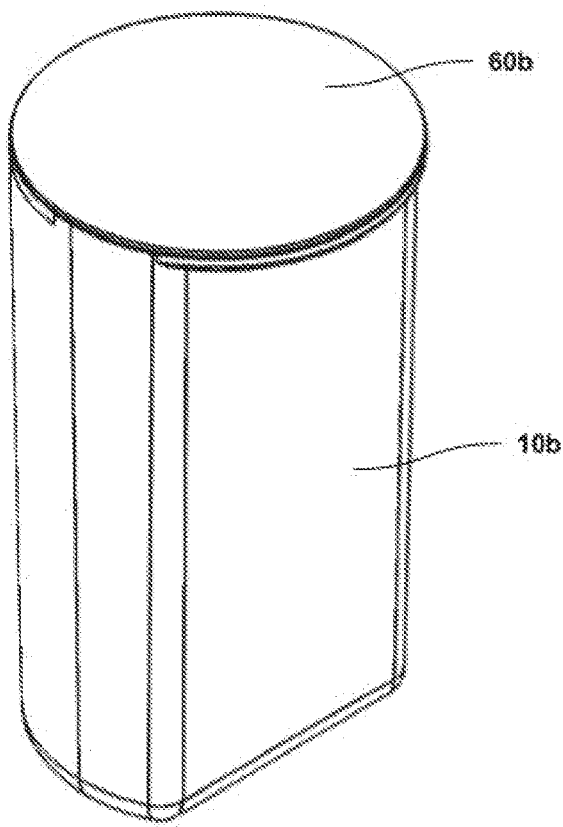

FIG. 10B illustrates the cartridge 10*b* that has been closed or sealed with the liner 60*b*.

FIG. 11A illustrates a snap-fitting feature 80*b* outside the cartridge 70*b* to allow a rigid attachment with the medication container. The snap-fitting feature 80*b* can be a raised ridge that extends around a circumference of cartridge 70*b*. The cartridge 70*b* can be same as or similar to the cartridge 10*b*. In some implementations, the same or a similar snap-fitting feature 80*b* can be provided on cartridges 30*b* and 40*b*.

FIG. 11B illustrates the cartridge 70*b* with the snap-fitting features 80*b* being inserted within the smart medication container 20*b*.

FIG. 11C illustrates the mechanism of the snap-fitting feature 80*b* enabling the snapping between the cartridge 70*b* and the medication container 20*b*. During vertical installation of the cartridge 70*b* into the medication container 20*b*, the snap-fit feature 80*b* can elastically deform, and then snap into corresponding geometry on the inside of the medication container 20*b*. The snap-fit features 80*b* can retain the cartridge 70*b* inside the smart medication container 20*b*, preventing the cartridge 70*b* from falling out or loosening. To vertically remove the insert 70*b* out of the medication container 20*b*, a force must be applied, manually or mechanically, to elastically deform the snap-fitting features 80*b*.

Figure 12B:
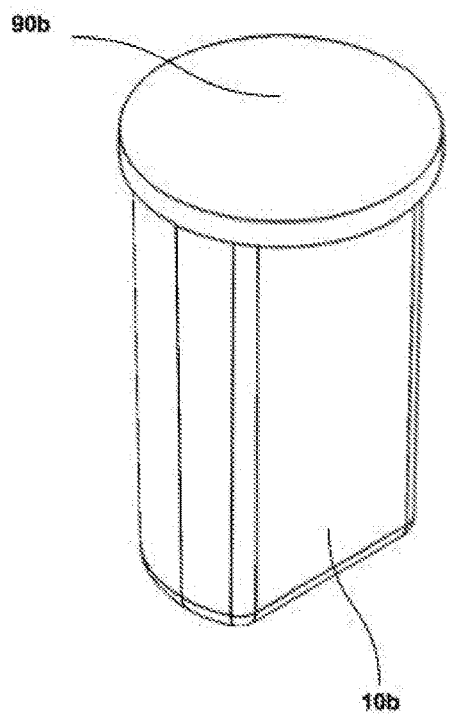
Figure 12A:
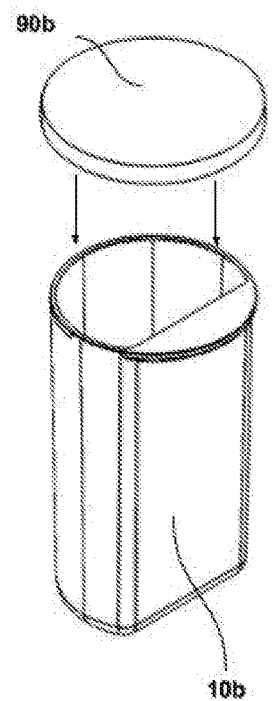

FIG. 12A illustrates a cap 90*b* having geometry that enables the cap 90*b* to elastically deform and snap to an outside of the cartridge 10*b* in order to seal or close the cartridge 10*b*. The sealing or closing of the cartridge 10*b* can prevent the contents within the cartridge 10*b* from falling out. The cap 90*b* can include features, such as a flap or tab, that can assist in removal of the cap 90*b* from the cartridge 10*b* by a user. The cap 90*b* can need to be removed in order to refill the contents of the cartridge 110*b*. The cap 90*b* can thus enable the cartridge 10*b* to act as a stand-alone container for medication. The cap 90*b* can also provide space for placing a label identifying the contents within the cartridge 10*b*. The cap 90*b* can be made of same or similar material as that forming the cartridge 10*b*. For example, the cap 90*b* can be made of made of plastics such as low-density polyethylene (LDPE), high-density polyethylene (HDPE), polypropylene (PP), other plastics, any other materials, and/or any combination thereof. In some implementations, the cap 90*b* can include features that resist tampering by children. In some implementations, the same or a similar cap 90*b* can be provided for closing cartridges 30*b* and 40*b*.

FIG. 12B illustrates the cartridge 10*b* sealed or closed with the cap 90*b*.

Figure 12C:
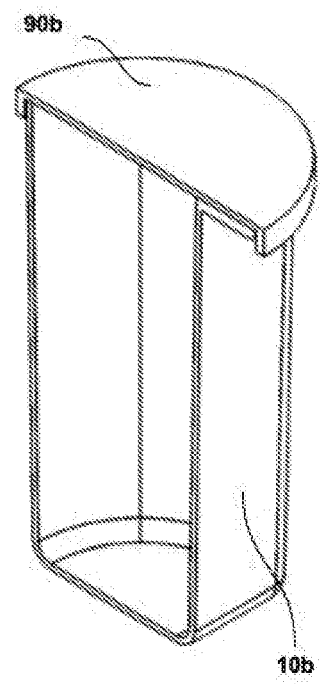

FIG. 12C illustrates a vertical cross-section of the cartridge 10*b* sealed or closed with the cap 90*b*.

Figure 13A:
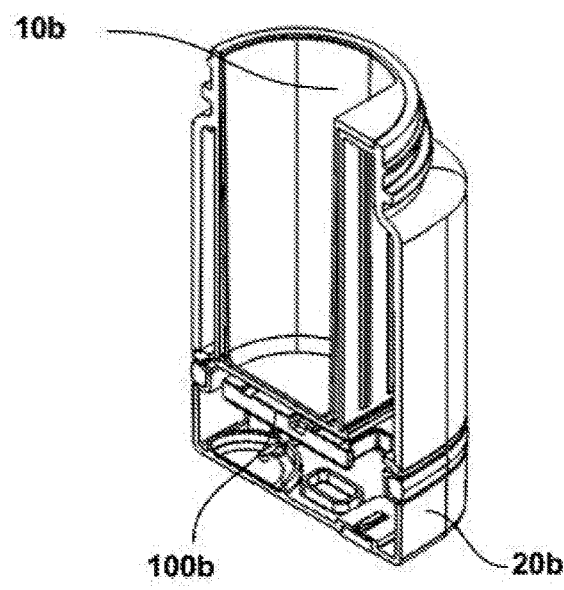

FIG. 13A illustrates one or more (e.g., an array of) sensors 100*b* inside the smart medication container 20*b*. The sensor array 100*b* can detect, for example, whether the cartridge 10*b* is present in and/or absent from the medication container 20*b*, and in some implementations can identify a unique serial number for the cartridge 10*b*. The sensor array 100*b* can be a radio frequency identifier (RFID) sensor. The RFID sensor can include an RFID label on the cartridge 10*b* and a near field reader in the medication container 20*b*. The RFID sensor can advantageously be small, inexpensive, and disposable. Although the RFID sensor is described, in alternate implementations other sensors can be used such as one or more of capacitance sensors, ultrasonic sensors, infrared sensors, strain gauges, magnetic sensors, one dimensional (1D) and two dimensional (2D) barcode scanning, near field communications (NFC), other sensors, RFID sensors, and/or any combination thereof.

Figure 13B:
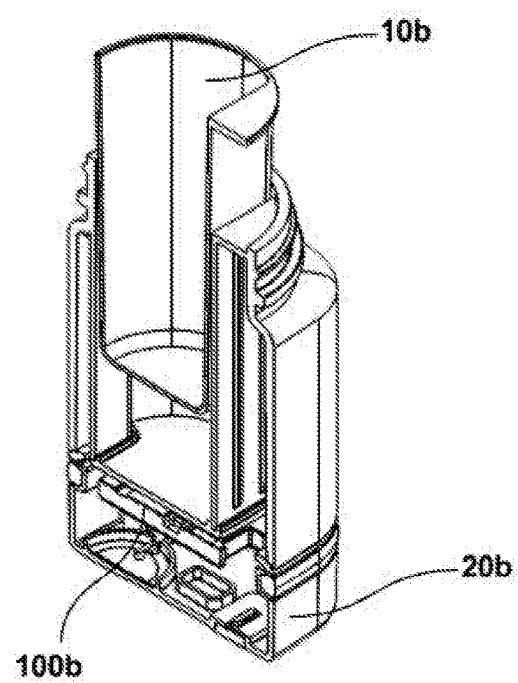

FIG. 13B illustrates the cartridge 10*b* being removed or installed in the medication container 20*b*, which includes the array of sensors 100*b*.

Figure 13C:
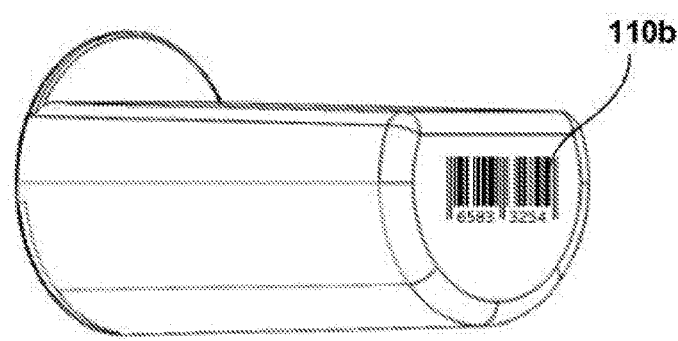

FIG. 13C illustrates the unique serial number 110*b* for the cartridge 10*b*, which can be shown and visible on the surface (e.g., for reading by a barcode reader) or, in some implementations, embedded in a readable device (e.g., RFID tag) for reading by a corresponding sensor.

Figure 14A:
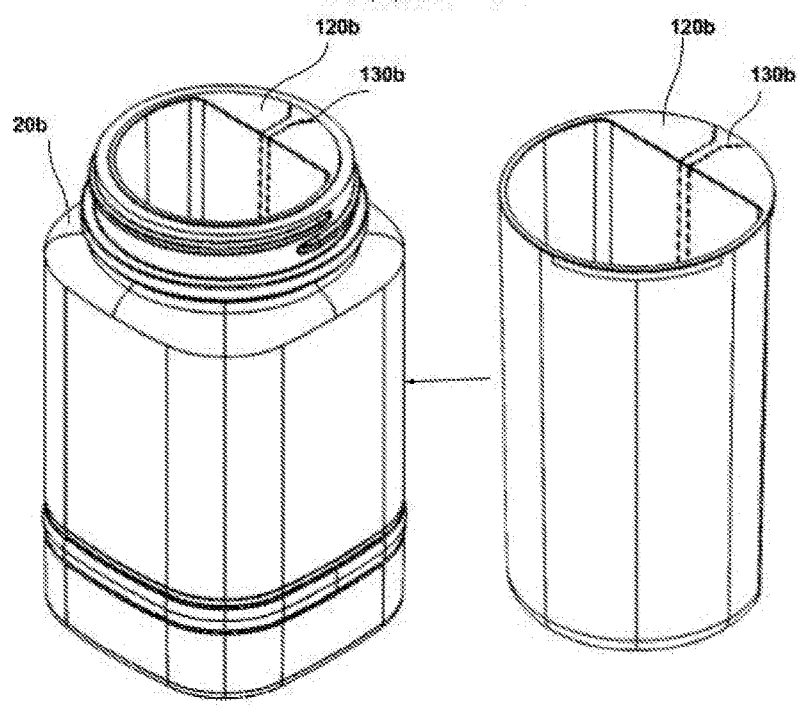

FIG. 14A illustrates a perforation feature 130*b* that is a part of the cartridge 120*b*. The perforation feature 130*b* can allow for an easy removal of the cartridge 120*b* from the smart medication container 20*b*. After the perforation feature 130*b* is cut or otherwise removed completely, the cartridge 120*b* can flex and shrink in size for easy removal. The perforation feature 130*b* can extend along the length, such as a partial length or alternately the entire length, of the cartridge 120*b*. The perforation feature can include an array of holes or slots oriented in the direction of the cartridge 120*b*. In some implementations, the perforation feature 130*b* can pierce through the wall of the cartridge 120*b*. In some implementations, the same or a similar perforation feature 130*b* can be provided on cartridges 30*b* and 40*b*.

Figure 14B:
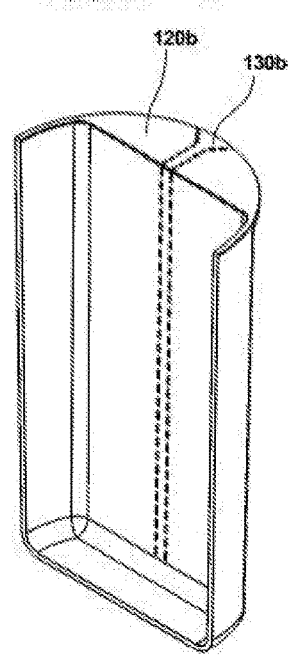

FIG. 14B illustrates a vertical cross-section of cartridge 120*b* with the perforation feature 130*b*.

Figure 15A:
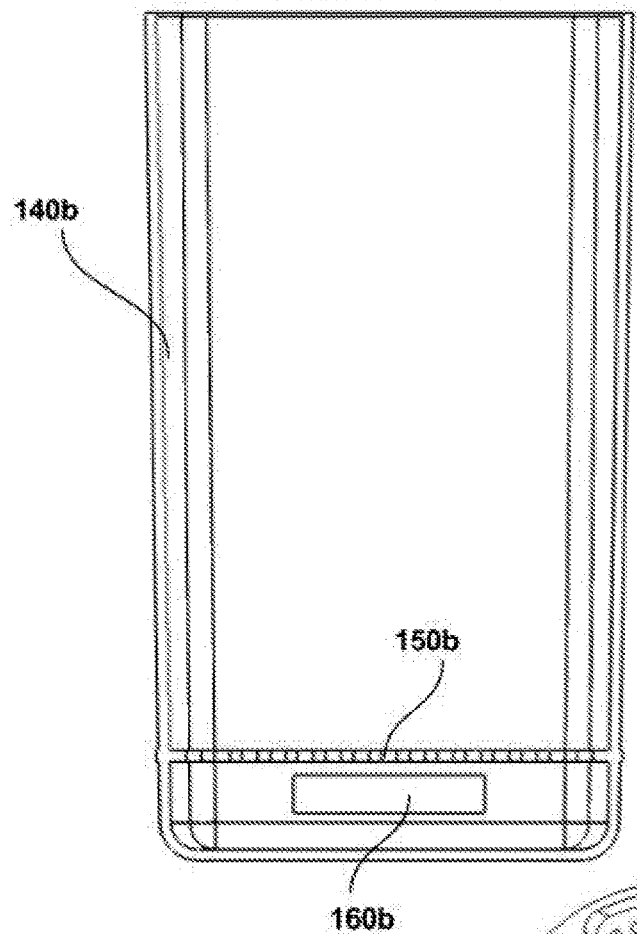

FIG. 15A illustrates a cartridge 140*b* with desiccant chamber 150*b* and internally stored one or more desiccant packets 160*b*. The desiccant chamber 150*b* can be an integral part of the cartridge 140*b*. In one implementation, the desiccant chamber 150*b* can include the desiccant packet (s) 160*b*. In another implementation, the desiccant chamber 150*b* can be separate from the desiccant packets 160*b*. The desiccant chamber 150*b* can include perforations, which can allow moisture to pass from the medication container 20*b* and/or the interior of cartridge 140*b* into the desiccant packet 160*b* while physically separating the contents of the cartridge 140*b* (e.g., medication stored within the cartridge 140*b*) from the desiccant packet 160*b*. In some implementations, the same or a similar desiccant chamber 150*b* and/or desiccant packet(s) can be provided within cartridges 30*b* and 40*b*.

Figure 15B:
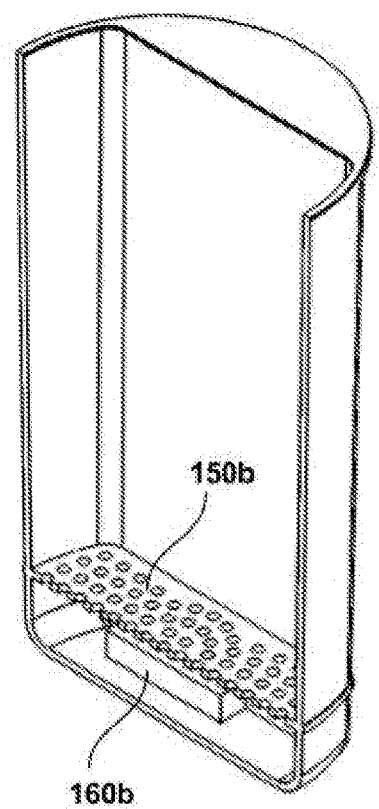

FIG. 15B illustrates a perspective view of a vertical cross-section of the cartridge 140*b* with desiccant chamber 150*b* and internally stored desiccant packet 160*b*.

Figure 15C:
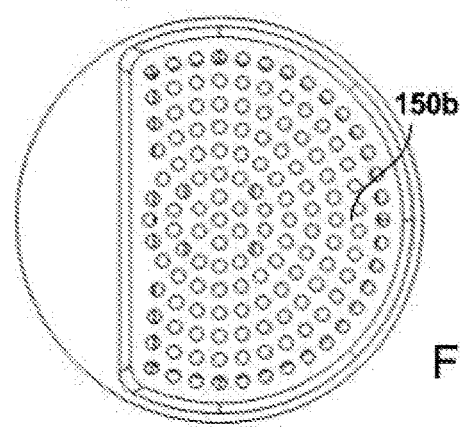

FIG. 15C illustrates a top view of a horizontal cross-section of the cartridge 140*b* showing the desiccant chamber 150*b*, which is physically above the desiccant packet 160*b*.

FIGS. 16A-16E and 17A-17E illustrate some implementations of a smart cap of a medication container according to some implementations of the current subject matter.

Figure 16A:
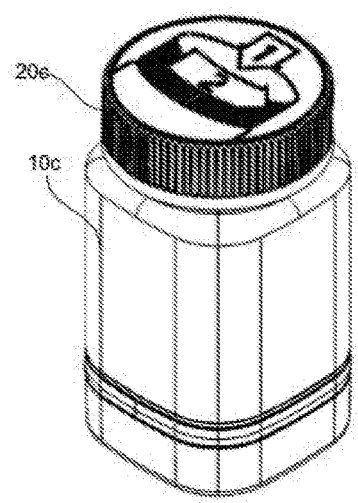
FIGS. 16A-16E and 17A-17E illustrate some implementations of a smart cap of a medication container according to some implementations of the current subject matter.

FIG. 16A illustrates a medication container 10*c* and a cap 20*c* thereof. In some implementations, the medication container 10*c* can be the same or similar to medication container 20*b*.

Figure 16B:
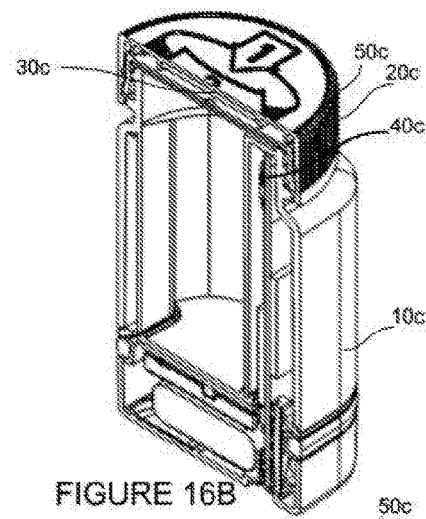

FIG. 16B illustrates a vertical cross-section of the medication container 10*c* with the cap 20*c* thereon, which further shows a cap sensor 30*c* and a container sensor 40*c*. In some implementations, the container sensor 40*c* can detect whether the cap sensor 30*c* is present within a threshold distance (e.g., a threshold distance from the container sensor 40*c* at the top or a point near the top of the medication container 10*c*). For example, this threshold distance can be approximately 0.125 inches, but can be larger or smaller in other implementations. The cap sensor 30*c* can be a magnet inside the cap, and can be detected by the container sensor 40*c*.

The cap sensor 30*c* can be inserted and located in a cavity underneath the exterior surface 50*c* of the cap 20*c*. An interior element 60*c* of the cap 20*c* is then inserted underneath the cap sensor 30*c* such that the cap sensor 30*c* is covered from above and below, as described with respect to FIG. 16D below.

The cap sensor 30*c*, alone or in combination with the container sensor 40*c*, can implement one or more of capacitance sensing, magnet and reed switch technology, ultrasonic distance sensing, strain-gauge deflection sensing, any other sensing technology, and any combination thereof. The container sensor 40*c*, alone or in combination with the cap sensor 30*c*, can implement one or more of capacitance sensing, magnet and reed switch technology, ultrasonic distance sensing, strain-gauge deflection sensing, any other sensing technology, and any combination thereof. In one implementation, the cap sensor element 30*c* and the container sensor element 40*c* can implement the same or similar sensing technology such that they act together to detect an event such as opening and/or closing of the cap and/or an amount of time the cap remains open and/or closed. The cap sensor 30*c* and the container sensor 40*c* may not implement different sensing technologies to avoid redundancy, as the cap sensor 30*c* and container sensor 40*c* act in unison. In some implementations, the container sensor 40*c* can also detect the quantity of medication remaining in the container 10*c*.

The cap 20*c* in some implementations can also be referred to as a smart cap. In such implementations, the cap 20*c* can include circuitry including a network interface, at least one programmable processor, a database, an electronic transmitter, and/or any other circuitry for communicating with a server computer 240*a* via a communication network 290*a* or 300*a*, as described in detail below in connection with FIG. 18. Alternatively or additionally, in some implementations, some or all of the circuitry for communicating with a remote server can be included within a body of the medication container 10*c* instead of the cap 20*c*.

Figure 16C:
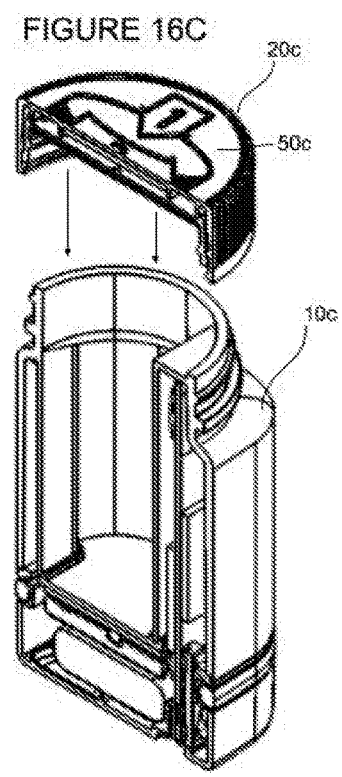

FIG. 16C illustrates a vertical cross-section of the medication container 10*c* with the cap 20*c* being separate from the medication container 10*c*.

Figure 16E:
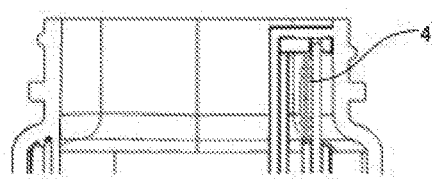
Figure 16D:
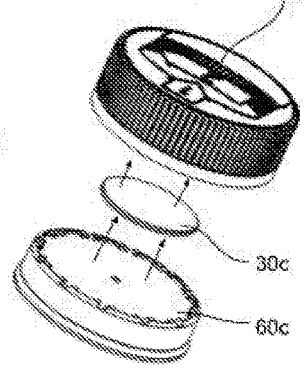

FIG. 16D illustrates that the cap sensor 30*c* can be inserted and located in a cavity underneath the exterior surface 50*c* of the cap 20*c*, and an interior element 60*c* of the cap 20*c* is then inserted underneath the cap sensor 30*c* such that the cap sensor 30*c* is covered from above and below.

FIG. 16E illustrates a close-up of the container sensor 40*c* showing that in some implementations it can be positioned in a region of the medication container that is adjacent to one or more features (e.g., threading or ridges) for receipt of cap 20*c*.

Figure 17A:
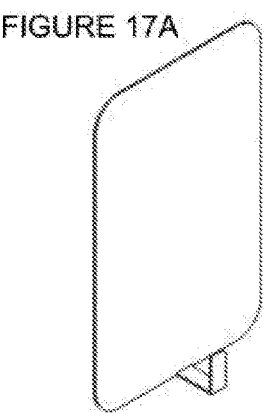

FIG. 17A illustrates a pull-tab component 70*c* configured to couple with the medication container 10*c*. The pull-tab component 70*c* can include one or more features (e.g., tabs or tails) for insertion within a battery compartment of the medication container 10*c*. The pull-tab component 70*c*, when inserted within medication container 10*c*, can function to prevent medication container 10*c* from drawing power from a battery within medication container 10*c*. For example, the one or more tabs inserted within container 10*c* can physically separate the battery from one or more battery terminals of the medication container 10*c*.

Figure 17B:
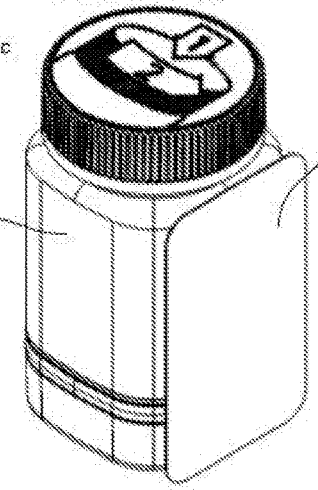

FIG. 17B illustrates the pull-tab component 70*c* coupled with the medication container 10*c*.

Figure 17C:
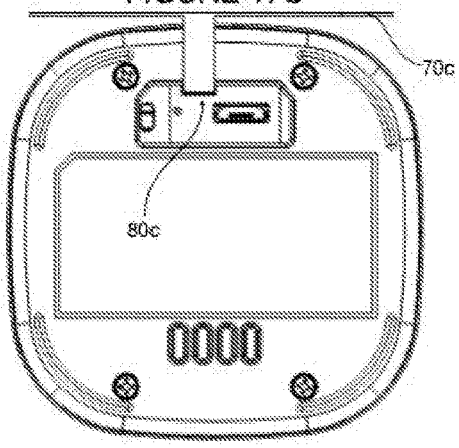

FIG. 17C illustrates another view of the pull-tab component 70*c* coupled with the medication container 10*c*. The pull-tab component 70*c* can be configured to deactivate or activate the medication container 10*c* through insertion and removal, respectively, of its tab or tail 90*c* (as shown in FIG. 17C) into a slot 80*c* on the medication container 10*c*.

Figure 17E:
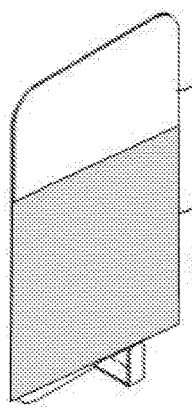
Figure 17D:
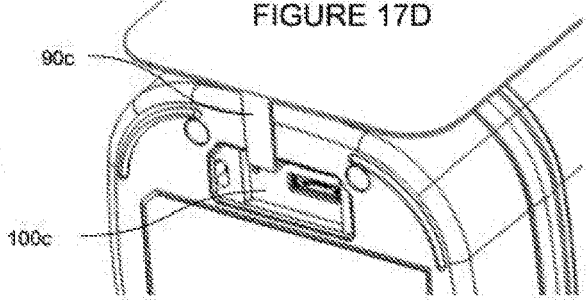

FIG. 17D illustrates yet another view of the pull-tab component 70*c* coupled with the medication container 10*c*. The smart medication container 10*c* can have a bottom cover 10, which can include a device that receives the tail 90*c* of the pull-tab 70*c*. The pull-tab component 70*c* can be configured to display information including instructions for using the medication container 10*c* and/or pull-tab component 70*c*, and/or information identifying the contents of the medication container 10*c*, and/or any other information.

The pull-tab component 70*c* can be made of one or more of plastics, paper, any other material, and any combination thereof. In one implementation, information can be printed on all surfaces of the pull-tab component 70*c*. In an alternate implementation, information can be printed on only selective surfaces of the pull-tab component 70*c*, such as only the exterior surface.

FIG. 17E illustrates an alternate pull-tab component 110*c* that can be configured to couple with the medication container 10*c*. The pull-tab component 110*c* can include one or more features, such as a pocket 120c on the pull-tab component 110c, that can allow the medication container 10c to hold additional information. The pocket 120c can be an integral or folded-up section of the pull-tab component 110c, or an additional part adhered to the original pull-tab component 11. Multiple materials, such as physical documents, written materials, information packets, other hardware, and/or the like, can be inserted into the pocket 120c.

Figure 18:
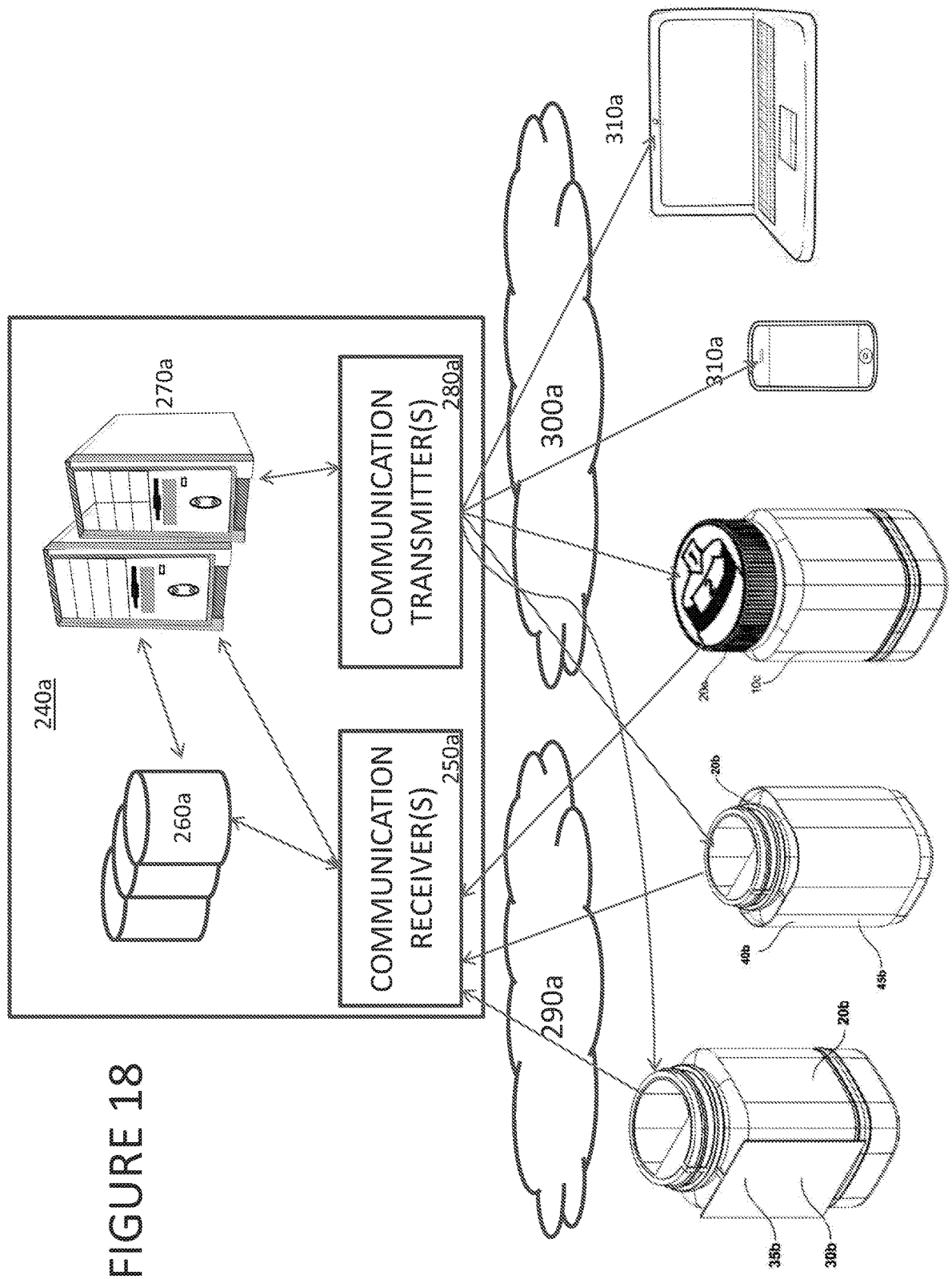
FIG. 18 illustrates a server computer that can communicate with circuitry on a medication container to generate reminders and/or alerts for a patient, a caregiver, a pharmacy, any other individual or entity, and/or any combination thereof.

FIG. 18 illustrates a server computer that can communicate with circuitry on a medication container (e.g., one or more medication containers shown and described in connection with FIGS. 7A-17E, each of which may include one or more processors, one or more sensors, and one or more electronic transmitters including at least a network interface, such as, for example, the medication containers shown in FIGS. 7A, 8A, 13A, and 16A) to generate reminders and/or alerts for a patient, a caregiver, a pharmacy, any other individual or entity, and/or any combination thereof. The server computer 240a can be remote to the medication container (e.g., medication container 20b or 10c), such as in a different room within a same building, a different building, a different city, a different state, a different country, or any remote distance. The communication network 290a or 300a can be one or more of a local area network, a wide area network, internet, intranet, Bluetooth network, infrared network, any other network, and any combination thereof. In various implementations, the server computer 240a may be in two-way communication with the medication container and/or one or more other computers (e.g., one or more computers 310a).

In various implementations, the at least one communication receivers 250a of the server computer 240a can be configured to receive data via the first communication network 290a from circuitry on one or more medication containers described herein (e.g., medication containers 10c and 20b). Such data can be, for example, data corresponding to one or more measurements of one or more of the sensors described herein, such as one or more sensor measurements indicating opening or closing of a cap medication container, one or more sensor measurements indicating whether one or more cartridges (e.g., cartridge 10b) is present within one a medication container (e.g., measurement(s) indicating whether a cartridge has been inserted to and/or removed from the medication container), one or more sensor measurements indicating a quantity of medication within a cavity of a medication container or one or more cartridges (e.g., cartridge 10b) of a medication container, and/or timing data identifying the timing of such detections by the one or more sensors. Based at least in part on the receipt of such data, and/or other data (e.g., historical data stored by or otherwise accessible to the server computer in a database 260a, such as data indicating one or more previous measurements received by the one or more sensors and/or timing data associated with the same), the server computer including one or more processors 270a may determine whether at least one criterion is satisfied and based on the determination trigger one or more reminders and/or alerts to a patient, a caregiver, and/or other entity (e.g., a pharmacy). For example, such alerts, which can include text, audio, imagery, video, or any combination thereof, may be transmitted to the medication container(s) themselves (e.g., medication containers 10c and 20b) and/or to other computing devices (e.g., computing devices 310a).

In some implementations, the communication network can receive data from a medication container (e.g., medication container 10c and 20b) indicating that one or more of medication containers 10c and/or 20b is in need of a refill of medication. In some implementations, the communication network can receive data from a medication container (e.g., medication container 10c and 20b) indicating that a patient has or is likely to have missed a dose of medication.

In one aspect, the at least one communication receiver 250a can be configured to receive, via a first communication network 290a and from the circuitry within the cap (e.g., cap 20c) and/or the body of the medication container (e.g., medication container 10c and 20b), data indicating that a preset amount of content within the medication container 10c was not withdrawn within a preset amount of time. The at least one database 260a can be configured to store at least the data. The at least one programmable processor 270a can determine, upon the receiving of the data, whether at least one criterion is satisfied, the at least one programmable processor 270a generating an alert when the at least one criterion is satisfied. The at least one communication transmitter 280a can be communicatively coupled to the at least one programmable processor 270a. The at least one communication transmitter 280a can be configured to transmit, via a second communication network 300a, the alert to a computing device 310a and/or to the medication container itself.

The indication that the preset amount of content within the medication container (e.g., medication container 10c and 20b) was not withdrawn can indicate that a dose of medication contained within the medication container was missed within the preset amount of time by a patient. The computing device 310a is one of a desktop computer, a laptop computer, a tablet computer, a phablet computer, and a cellular phone. In one implementation, the computing device 310a can be configured to be operated by a patient using the medication container. In another implementation, the computing device 310a can be configured to be operated by at least one of: a caregiver (e.g., hospital, clinician, doctor, nurse, technician, clinical staff member, and/or any other caregiver) treating a patient using the medication container 10c, a pharmacy authorized to provide medication to the patient, and a healthcare company authorized to obtain healthcare data of the patient.

In one implementation, the satisfying of the at least one criterion can be a risk level of a user exceeding a threshold value. The at least one programmable processor 270a can compute the risk level based at least in part on historical data stored in the database 260a, in a manner that is similar to or the same as the manner described above in connection with, for example, FIG. 6C. For example, the historical data used by the at least one processor 270a to determine a risk level can include one or more of: data indicative of prior measurements of one or more sensors of the medication container (e.g., medication container 10c and 20b), a pattern of withdrawing medication from the medication container, a pattern of refilling the medication container, a type of medication in the medication container, a dosage requirement for consuming the medication, timing of one or more prior communications between the circuitry of the medication container and the at least one communication receiver 250a, data exchanged between the circuitry of the medication container and the at least one communication receiver 250a during the one or more prior communications, and one or more errors noted with respect to the one or more prior communications.

In another implementation, the satisfying of the at least one criterion can be lack of withdrawal of the preset amount of content within the medication container (e.g., medication container 10c and 20b) within another preset amount of time. The lack of withdrawal of the preset amount within the other preset amount of time can indicate that a dose of medication contained within the medication container was missed within the other preset amount of time. The data indicating the lack of withdrawal of the preset amount within the other preset amount of time can be stored in the database 260a. The at least one programmable processor 270a can determine the lack of withdrawal of the preset amount within the other preset amount of time by receiving from the database 260a the data indicating the lack of withdrawal of the preset amount within the other preset amount of time.

In yet another implementation, the satisfying of the at least one criterion can be the withdrawal of the preset amount of content within the medication container (e.g., medication container 10c and 20b) after the preset amount of time. The withdrawal of the preset amount of content within the medication container after the preset amount of time can indicate that a patient took the medication late. The at least one programmable processor 270a can be configured to receive, from the circuitry on the medication container, data indicating withdrawal of the preset amount of content within the medication container 10c. The at least one programmable processor 270a can identify a time of the receiving of the data indicating the withdrawal to determine whether the withdrawal is after the preset amount of time.

In another implementation, the satisfying of the at least one criterion can be a refilling of medication container (e.g., medication container 10c and 20b) after a preset amount of time. The refilling of the medication container 10c after the preset amount of time can indicate that the refilling of the medication container 10c was late. The at least one programmable processor 270a can be configured to receive, from the circuitry on the medication container, data indicating the refilling of the medication container. The at least one programmable processor 270a can identify or determine a time of the refilling of the medication container to determine whether the refilling was late.

The alert, as described herein, can be data that activates an alarm, which can be audio, visual, or both. In various implementations, the alert can be one or more of: a text message, a voice message, a video message, a social media message, an email, a web pop-up, a pager message, any other message, and any combination thereof. The alert can be a reminder in some implementations.

In another aspect, the at least one communication receiver 250a can be configured to receive, via a first communication network 290a and from circuitry on a medication container (e.g., medication container 10c and 20b), data indicating that medication container was not refilled within a preset amount of time. The at least one programmable processor 270a can be configured to generate an alert upon the receiving of the data. The at least one communication transmitter 280a can be configured to transmit, via a second communication network 300a, the alert to a computing device 310a and/or to the medication container itself.

In one implementation, the computing device 310a can be configured to be operated by a patient. In another implementation, the computing device 310a can be configured to be operated by at least one of: a caregiver treating the patient, a pharmacy authorized to provide medication to the patient, and a healthcare company authorized to obtain healthcare data of the patient.

In another aspect, the at least one communication receiver 250a can be configured to receive a message from a first computing device 310a via a first communication network 290a. The at least one programmable processor 270a can generate an alert upon the receiving of the message. The at least one communication transmitter 280a can be configured to transmit, via a second communication network 300a, the alert to a second computing device 310a.

The first computing device 310a can be configured to be operated by a patient. The second computing device 310a can be configured to be operated by at least one of: a caregiver treating the patient, a pharmacy authorized to provide medication to the patient, and a healthcare company authorized to obtain healthcare data of the patient. In one implementation, the message can include a request for additional care.

In some implementations, the at least one processor 270a is configured to determine that a patient has not adhered to a medication regimen and/or that a medication container or cartridge within a medication container (e.g., medication container 10c and/or 20b) has not been refilled according to an expected schedule based at least in part on the at least one processor 270a not receiving a communication from the medication container within a preset amount of time. For example, the at least one processor 270a can trigger an alert (e.g., reminder) to the medication container (e.g., medication container 10c and/or 20b) and/or another one or more computing devices based at least in part on the at least one processor 270a identifying that the one or more cartridge sensors and/or one or more container and/or cap sensors of the medication container have not been activated within a period of time that exceeds a preset amount of time. The preset amount of time can be set or identified by the at least one processor 270a based at least in part on data stored in database 260a and accessible to the at least one processor 270a indicating: a medication regimen for a patient that identifies an expected frequency of the patient taking a dose; and/or an expected refill schedule for the medication container or a cartridge contained within the medication container. The at least one processor 270a can compare this data, for example, to data indicating the last time the at least one processor 270a received a communication from the one or more sensors of the medication container to determine if the preset amount of time has lapsed without at least one processor 270a receiving a further one or more communications from one or more sensors of the medication container. Based at least in part on (e.g., based solely on) the determination, the at least one processor 270a can trigger one or more alerts to the medication container (e.g., medication container 10c and/or 20b) and/or another one or more computing devices 310a.

TABLE 1 below identifies various implementations of one or more criteria that can be utilized by the at least one processor 270a of a server computer, shown in FIG. 6C and/or FIG. 18, to trigger an alert (e.g., reminder) to a medication container and/or one or more other computing devices 310a. In these various implementations, where only one triggering criterion is identified (labeled as "A"), the at least one processor 270a need only determine that this triggering criterion is satisfied to produce to cause the corresponding identified event. Where two items are identified as triggering criteria (labeled as "A" and "B"), in some implementations the at least one processor 270a produces or causes the corresponding identified event only after the at least one processor 270a determines that both triggering criteria are satisfied. Other variations are possible. In some implementations, the at least one processor 270a evaluates one or more criteria in addition to the criteria identified below.

TABLE 1

| Example | One or More Triggering Criteria | Event |
|---|---|---|
| 1 | A. System receives notification from medication container that dose was missed<br>B. System determines that user of medication container is high-risk based on one or more of multiple data points from previous analysis (e.g. overall adherence score, complex dosage pattern, inaccurate dosing or refill patterns, medication information, previous messaging to the system) | System sends specialized alert to medication container and/or user computer(s) associated with the bottle |
| 2 | A. System receives notification from medication container that dose was missed<br>B. System determines that user of medication container is high-risk based on one or more of multiple data points from previous analysis (e.g. overall adherence score, complex dosage pattern, inaccurate dosing or refill patterns, medication information, previous messaging to the system) | System sends specialized alert to computers of caregiver, care team, pharmacy, or healthcare company |
| 3 | A. System receives notification from medication container that dose was missed<br>B. System determines that one or more recent doses was also missed | System sends specialized alert to medication container and/or user computer(s) associated with the bottle |
| 4 | A. System receives notification from medication container that dose was missed<br>B. System determines that one or more recent doses was also missed | System sends specialized alert to computers of caregiver, care team, pharmacy, or healthcare company |
| 5 | A. System receives notification from medication container that dose was missed<br>B. System determines that a user or entity is late starting or restarting the planned medication/refill cycle | System sends specialized alert to medication container and/or user computer(s) associated with the bottle |
| 6 | A. System receives notification from medication container that dose was missed<br>B. System determines that a user or entity is late starting or restarting the planned medication and/or medication refill cycle | System sends specialized alert to computers of caregiver, care team, pharmacy, or healthcare company |
| 7 | A. Medication container one or more sensors measure that medication container was not refilled | System sends specialized alert to medication container and/or user computer(s) associated with the bottle |
| 8 | A. medication container one more sensors measure that medication container was not refilled | System sends specialized alert to computers of caregiver, care team, pharmacy, or healthcare company |
| 9 | A. System receives message from user or entity associated with medication container that additional care is required | System sends specialized alert to the medication container, user computer(s), and/or computers of caregiver, care team, pharmacy, or healthcare company |
| 10 | A. System receives message from user or entity associated with medication container having any content | System sends specialized alert to medication container, user computer(s), and/or computers of caregiver, care team, pharmacy, or healthcare company |

Any one or more implementations, aspects, or variations described herein can be combined if and when feasible. The terms substantially, almost, or generally, as used herein, can mean most in some implementations. In other implementations, the terms substantially, almost, or generally can refer to eighty percent or more of the entirety or regular value/measure/form. In another implementation, the terms substantially, almost, or generally can refer to ninety percent or more of the entirety or regular value/measure/form. In some implementations, the terms substantially, almost, or generally can refer to ninety five percent or more of the entirety or regular value/measure/form. In some implementations, the terms substantially, almost, or generally can refer to ninety five percent or more of the entirety or regular value/measure/form. The term matingly connected, and other similar terms, as used herein, can refer to a physical connection between two elements. In some implementations, such a connection can be enabled by coupling a male part of a first element of the two elements with a female part of a second element of the two elements.

Although several variations have been described in detail above, other modifications are possible. For example, the logic flows described in the patent application do not require the particular order shown, or sequential order, to achieve desirable results. Further, while preferred materials for elements of construction have been described herein the device is not limited by these materials. Plastics, rubber, foam, metal alloys, wood and/or other materials can be used to make some or all of the elements of the device.

Related apparatuses, systems, techniques and articles are also described. Computer program products are described that comprise non-transitory computer readable media storing instructions, which when executed by at least one programmable processors of one or more computing systems, causes at least one programmable processor to perform operations herein. Similarly, computer systems are also described that can include one or more programmable processors and a memory coupled to the one or more programmable processors. The memory can temporarily or permanently store instructions that cause at least one programmable processor to perform one or more of the operations described herein. In addition, methods can be implemented by one or more programmable processors either within a single computing system or distributed among two or more computing systems.

The terminology used herein is for the purpose of describing particular implementations and is not intended to be limiting the claims. As used herein, "and/or" includes any and all combinations of one or more described items. Use of terms such as "comprises" and/or "comprising" specifies the inclusion and presence of stated features, attributes, and components but does not preclude the inclusion or addition of one or more other features, attributes, and components.

As used herein, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." In addition, use of the term "based on," above and in the claims is intended to mean, "based at least in part on," such that an unrecited feature or element is also permissible. Further, as used herein, the singular terms "a," "an," and "the" can include the plural reference unless the context clearly indicates otherwise.

Unless otherwise defined, all terms used herein have the same meaning as commonly understood by one having ordinary skill in the art to which the invention belongs. The meaning of terms used in this description should be interpreted as having meaning consistent with their meaning in the context of the relevant art.

The present disclosure is to be considered as an exemplification of the claimed implementation(s) and is not intended to limit those implementations to the specific implementations illustrated by the figures.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can be have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (e.g., magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device (e.g., a display device of the medication container or cap), such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer (e.g., medication container) having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

The computing system can include clients and servers. A client and server can be generally remote from each other and can interact through a communication network. The relationship of client and server can arise by virtue of computer programs running on the respective computers and having a client-server relationship with each other.

Although several variations have been described in detail above, other modifications can be possible. For example, the logic flows depicted in the accompanying figures and described herein do not require the particular order shown, or sequential order, to achieve desirable results. That is, other sequential orders are possible. The description above for each drawing corresponds to a respective set of implementations, but other implementations can necessitate some modifications as understood by one of ordinary skill in the art. Those modifications are within the scope of this patent application. For the separate implementations described herein, in other implementations of the present disclosure components of any implementation can be incorporated in other implementations, as suitable. Such other implementations are within the scope of the claims.

What is claimed is:

1. An apparatus, comprising:
a container configured to be closed with a cap; and
a cartridge for housing medication configured to be inserted within the container, the cartridge when completely inserted within the container allowing the closing of the container with the cap;
the cap including a cap sensor element configured to detect whether the container has not been activated within a predetermined period of time;
the container generating an alert based on the cap sensor detecting whether the container has not been activated within the predetermined period of time and whether a preset quantity of medication has not been withdrawn from the cartridge at a preset time, the alert being generated based on:
an adherence score characterizing a likelihood of adherence of a patient to a medication regimen associated with the medication, the adherence score being determined based on:
weighting a consumption of the medication at a first time period in accordance with a first percentage, the first time period corresponding to a designated time frame for the consumption of the medication,
weighting an additional consumption of the medication at a second time period in accordance with a second percentage, the second time period is different from and independent of the designated time frame for the consumption of the medication, and wherein the first percentage is higher than the second percentage.

2. The apparatus of claim 1, wherein a body of the cartridge fits within a cavity within the container and a portion of the cartridge overlies a top of the container in a region where the container accepts the cap.

3. The apparatus of claim 1, wherein one or more locations on an outer surface of the cartridge include an adhesive that sticks to an inner surface of the container.

4. The apparatus of claim 1, wherein a portion of the cartridge extends externally to the container and is configured to serve as a grip for holding the container.

5. The apparatus of claim 1, wherein a portion of the cartridge extends externally to the container and is configured to serve as a display element.

6. The apparatus of claim 5, wherein the display element is configured to display data identifying content within the cartridge.

7. The apparatus of claim 6, wherein the display element comprises a printed label containing the data identifying the content within the cartridge.

8. The apparatus of claim 1, wherein the cartridge is configured to be closed with at least one of a plug and a liner, each of the plug and the liner being different and separate from the cap.

9. The apparatus of claim 8, wherein the cartridge is configured to be sealed by each of the plug and the liner to prevent content within the cartridge from falling out, each of the plug and the liner being removable from the cartridge.

10. The apparatus of claim 1, wherein the cartridge comprises a desiccant chamber and at least one desiccant packet, the desiccant chamber including perforations that allow moisture to pass from a body of the cartridge into the at least one desiccant packet and to physically separate content of the cartridge from the at least one desiccant packet.

11. The apparatus of claim 1, wherein the cap sensor element is configured to detect whether the container has not been activated within the predetermined period of time that exceeds a present amount of time.

12. The apparatus of claim 1, wherein the cap sensor element is configured to detect a quantity of content within the container.

13. The apparatus of claim 1, wherein the cap sensor element includes at least one of the following: a capacitance sensor, a magnet sensor, a reed switch sensor, an ultrasonic distance sensor, a strain-gauge deflection sensor, and any combination thereof.

14. The apparatus of claim 1, wherein the cap sensor element is configured to detect at least one of an opening of the cap and a closing of the cap.

* * * * *